United States Patent
Kipnis et al.

(10) Patent No.: US 11,312,775 B2
(45) Date of Patent: Apr. 26, 2022

(54) METHODS FOR TREATMENT OR PREVENTION OF A NEUROLOGICAL IMMUNITY DISORDER

(71) Applicant: University of Virginia Patent Foundation, Charlottesville, VA (US)

(72) Inventors: Jonathan Kipnis, Charlottesville, VA (US); Antoine Louveau, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/631,991

(22) PCT Filed: Jul. 19, 2018

(86) PCT No.: PCT/US2018/042955
§ 371 (c)(1),
(2) Date: Jan. 17, 2020

(87) PCT Pub. No.: WO2019/018688
PCT Pub. Date: Jan. 24, 2019

(65) Prior Publication Data
US 2020/0172624 A1    Jun. 4, 2020

Related U.S. Application Data

(60) Provisional application No. 62/534,895, filed on Jul. 20, 2017.

(51) Int. Cl.
| | | |
|---|---|---|
| C07K 16/28 | (2006.01) | |
| A61P 25/28 | (2006.01) | |
| A61K 39/00 | (2006.01) | |
| A61K 9/00 | (2006.01) | |

(52) U.S. Cl.
CPC .......... C07K 16/2842 (2013.01); A61P 25/28 (2018.01); A61K 9/0019 (2013.01); A61K 9/0085 (2013.01); A61K 2039/505 (2013.01)

(58) Field of Classification Search
CPC . C07K 16/2842; C07K 2317/76; A61P 25/28; A61K 9/0019; A61K 9/0085; A61K 2039/505; A61K 2039/54; A61K 2039/57; A61K 2039/545
See application file for complete search history.

(56) References Cited

U.S. PATENT DOCUMENTS

| | | | | |
|---|---|---|---|---|
| 7,910,099 | B2* | 3/2011 | Karpusas | A61P 19/04 |
| | | | | 424/130.1 |
| 2002/0146417 | A1 | 10/2002 | Gotwals et al. | |
| 2004/0081651 | A1* | 4/2004 | Karpusas | A61P 19/02 |
| | | | | 424/146.1 |
| 2006/0286112 | A1 | 12/2006 | Kellermann et al. | |
| 2007/0025989 | A1 | 2/2007 | Taylor et al. | |
| 2010/0272716 | A1* | 10/2010 | Karpusas | A61P 37/06 |
| | | | | 424/133.1 |
| 2016/0017043 | A1 | 1/2016 | Fowler et al. | |

FOREIGN PATENT DOCUMENTS

| | | |
|---|---|---|
| WO | 2002/022571 A2 | 3/2002 |
| WO | 2006/055871 A2 | 5/2006 |
| WO | 2007/140249 A1 | 12/2007 |
| WO | 2016/022656 A1 | 2/2016 |
| WO | 2019/018688 A1 | 1/2019 |
| WO | 2020/150214 A1 | 7/2020 |

OTHER PUBLICATIONS

Matricardi et al., Frontiers in Pediatrics, 7, article 511, Dec. 2019 (Year: 2019).*
Baker et al., Multiple Sclerosis Journal, 17(6):647-657, 2011 (Year: 2011).*
Keeley et al., Ann Pharmacother 39:1833-43, 2005 (Year: 2005).*
BD Biosciences Catalog No. 553961. Retrieved online. Retrieved from www.bdbiosciences.com/us/reagents/research/antibodies-buffers/immunology-reagents/anti-mouse-antibodies/cell-surface-antigens/purified-nale-hamster-igg2-1-isotype-control-ha48/p/553961; Retrieved on Jun. 4, 2021. (Year: 2021).*
Ajami et al., Single-cell mass cytometry reveals distinct populations of brain myeloid cells in mouse neuroinflammation and neurodegeneration models. Nat Neurosci. Apr. 2018;21(4):541-551.
International Search Report and Written Opinion for Application No. PCT/US2020/013477, dated May 7, 2020, 12 pages.
International Search Report and Written Opinion for Application No. PCT/US2018/042955, dated Sep. 25, 2018, 15 pages.
International Preliminary Report on Patentability for Application No. PCT/US2018/042955, dated Jan. 30, 2020, 8 pages.
Bank et al., Interaction of disease-related antigen-reactive T-cell lines from multiple sclerosis patients with type IV collagen: role of integrin VLA-1 and effects of irradiation. J Clin Immunol. May 2002;22(3):153-63.
Goldstein et al., alpha1beta1 Integrin+ and regulatory Foxp3+ T cells constitute two functionally distinct human CD4+ T cell subsets oppositely modulated by TNFalpha blockade. J Immunol Jan. 1, 2007;178(1):201-10.

(Continued)

*Primary Examiner* — Kimberly Ballard
*Assistant Examiner* — Stacey N Macfarlane
(74) *Attorney, Agent, or Firm* — McCarter & English, LLP; Marcie B. Clarke

(57) ABSTRACT

Methods of treating, preventing, inhibiting, delaying the onset of, or ameliorating a neurological immunity disorder can include administering an effective amount of a compound comprising an antibody or antigen binding fragment of an antibody to a subject in need of treatment, prevention, inhibition, delay of onset, or amelioration of a neurological immunity disorder. The antibody or the antigen binding fragment of an antibody binds specifically to CD49a.

5 Claims, 22 Drawing Sheets
Specification includes a Sequence Listing.

(56) References Cited

OTHER PUBLICATIONS

Schwab et al., Therapeutic uses of anti-a4-integrin (anti-VLA-4) antibodies in multiple sclerosis. Int Immunol. Jan. 2015;27(1):47-53.
Sobel et al., Endothelial cell integrin laminin receptor expression in multiple sclerosis lesions. Am J Pathol. Aug. 1998;153(2):405-15.

* cited by examiner

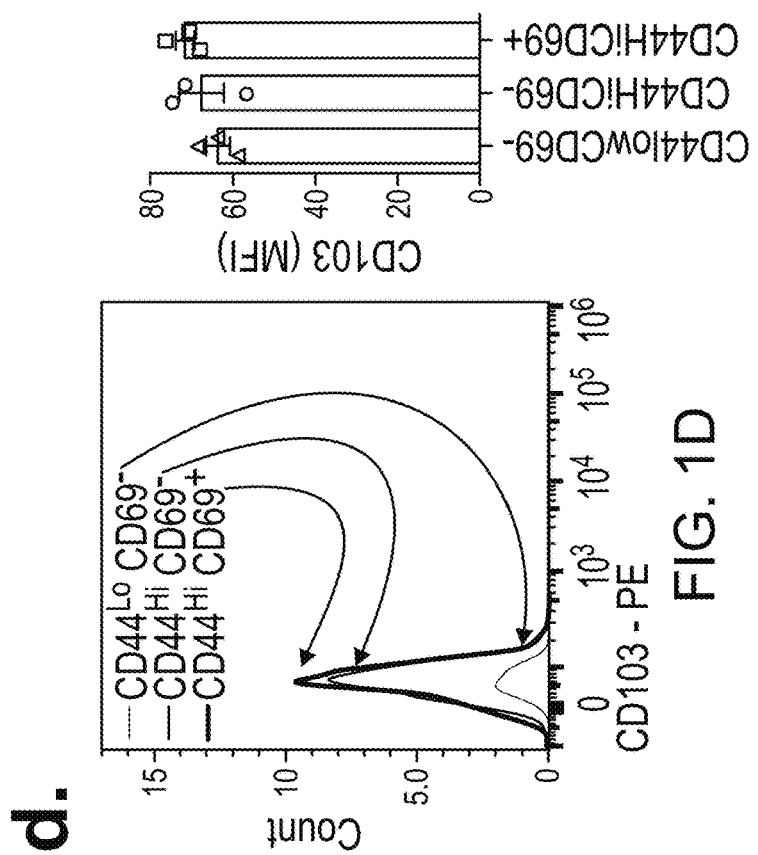
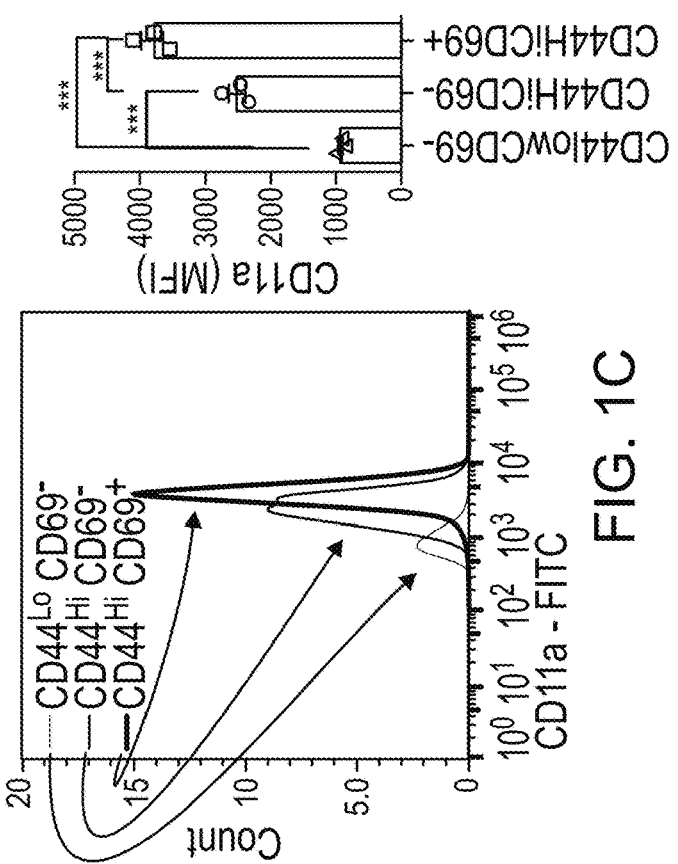
FIG. 1C
FIG. 1D

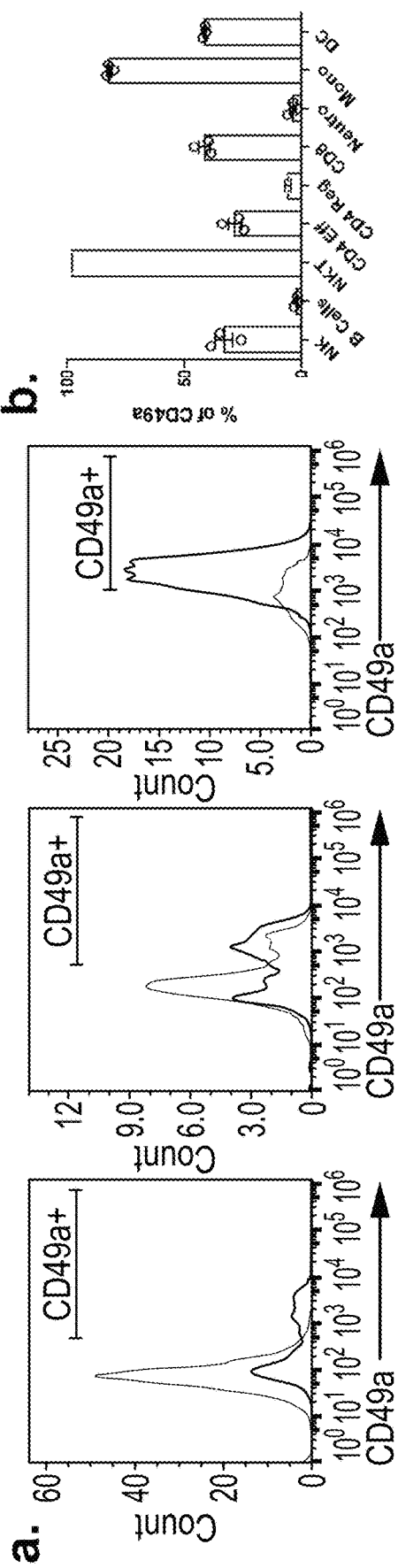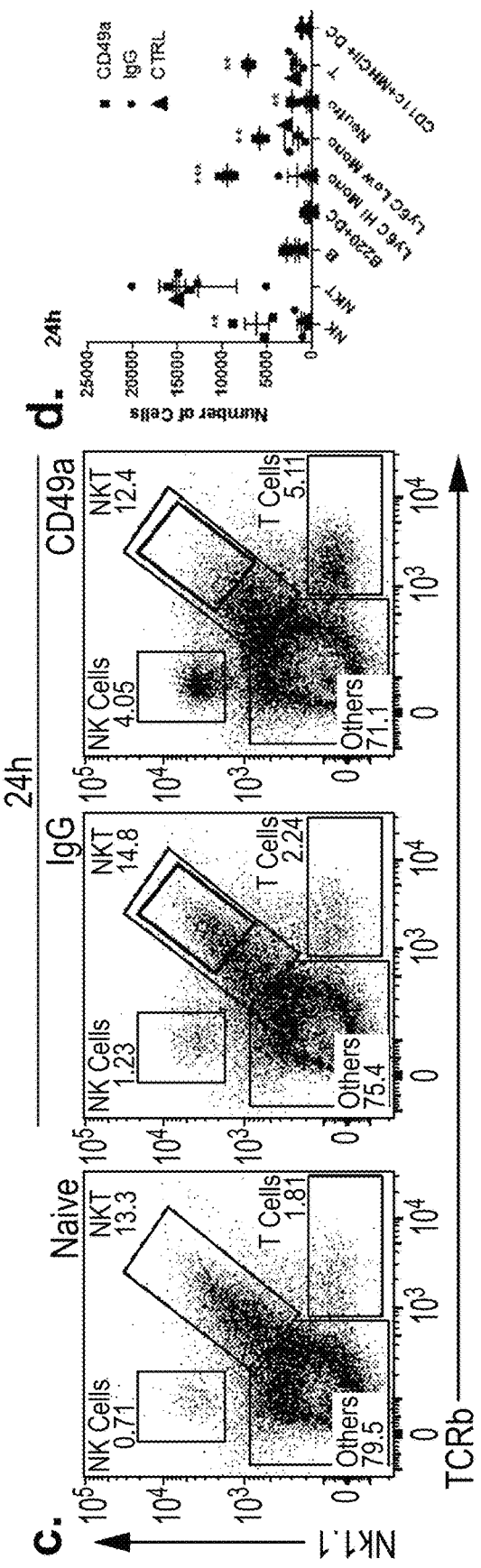

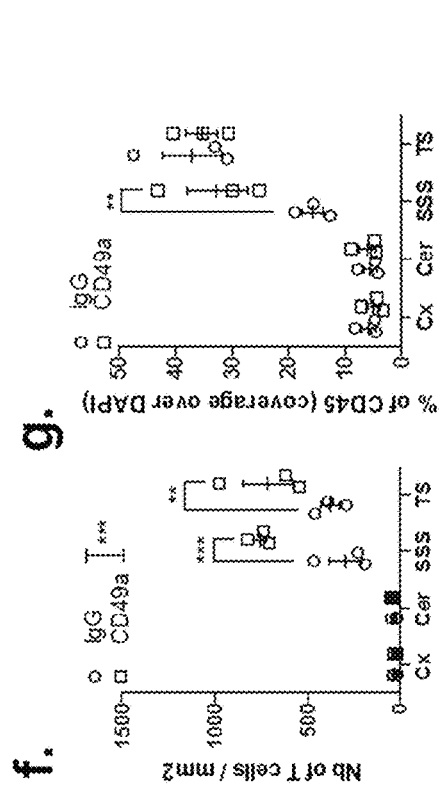
FIG. 2E
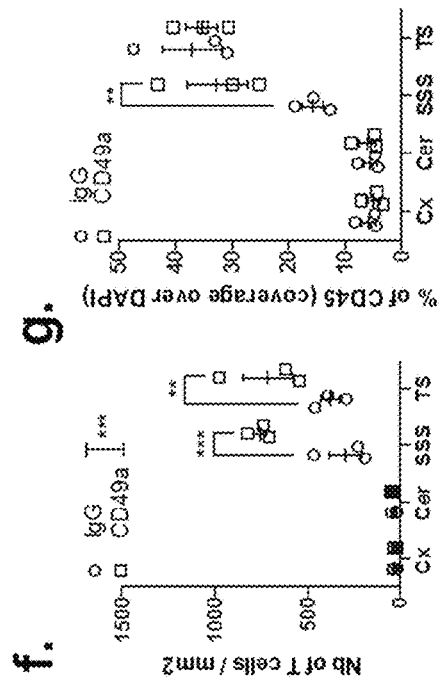
FIG. 2F
FIG. 2G
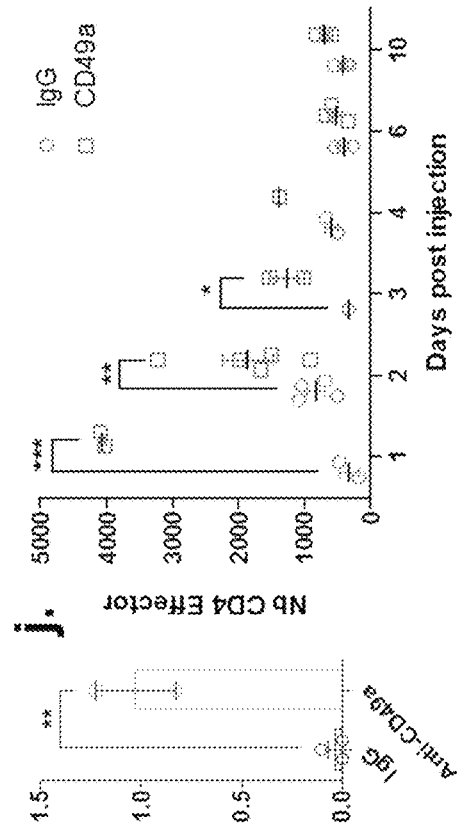
FIG. 2H
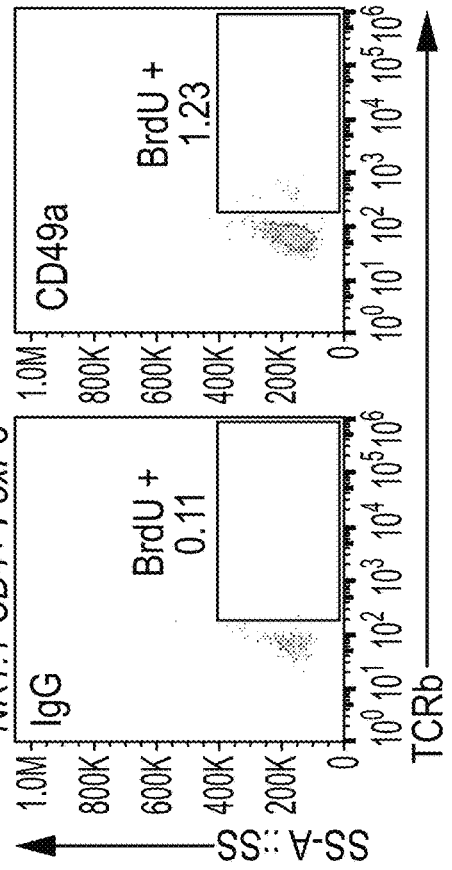
FIG. 2I
FIG. 2J

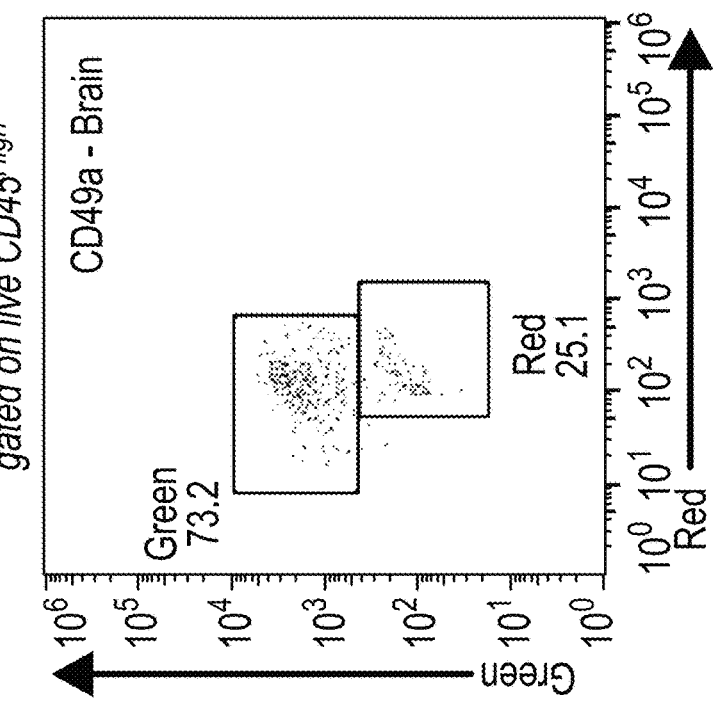
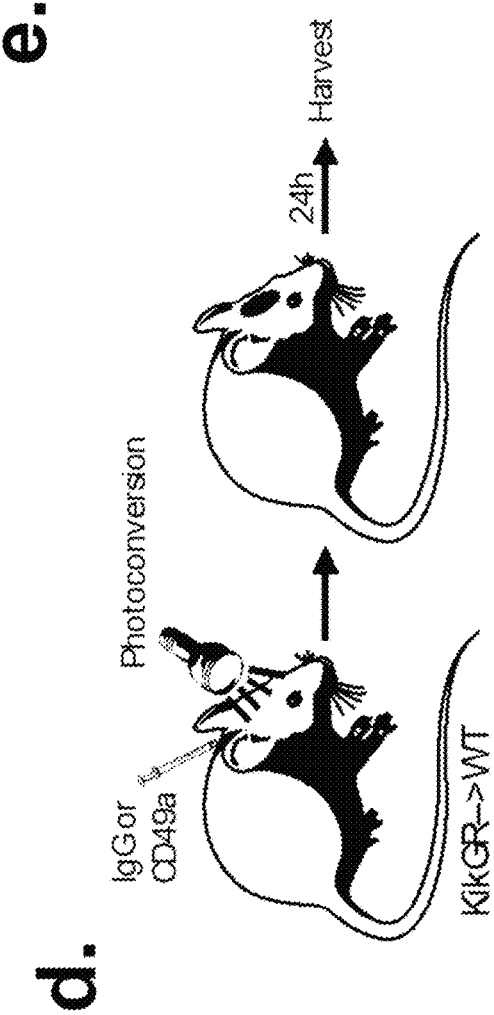
FIG. 4E
FIG. 4D

SEQUENCE LISTING

```
<160> NUMBER OF SEQ ID NOS: 3

<210> SEQ ID NO 1
<211> LENGTH: 1179
<212> TYPE: PRT
<213> ORGANISM: Homo sapiens

<400> SEQUENCE: 1

Met Ala Pro Arg Pro Arg Ala Arg Pro Gly Val Ala Val Ala Cys Cys
1               5                   10                  15

Trp Leu Leu Thr Val Val Leu Arg Cys Cys Val Ser Phe Asn Val Asp
            20                  25                  30

Val Lys Asn Ser Met Thr Phe Ser Gly Pro Val Glu Asp Met Phe Gly
        35                  40                  45

Tyr Thr Val Gln Gln Tyr Glu Asn Glu Glu Gly Lys Trp Val Leu Ile
    50                  55                  60

Gly Ser Pro Leu Val Gly Gln Pro Lys Asn Arg Thr Gly Asp Val Tyr
65                  70                  75                  80

Lys Cys Pro Val Gly Arg Gly Glu Ser Leu Pro Cys Val Lys Leu Asp
                85                  90                  95

Leu Pro Val Asn Thr Ser Ile Pro Asn Val Thr Glu Val Lys Glu Asn
            100                 105                 110

Met Thr Phe Gly Ser Thr Leu Val Thr Asn Pro Asn Gly Gly Phe Leu
        115                 120                 125

Ala Cys Gly Pro Leu Tyr Ala Tyr Arg Cys Gly His Leu His Tyr Thr
    130                 135                 140

Thr Gly Ile Cys Ser Asp Val Ser Pro Thr Phe Gln Val Val Asn Ser
145                 150                 155                 160

Ile Ala Pro Val Gln Glu Cys Ser Thr Gln Leu Asp Ile Val Ile Val
                165                 170                 175

Leu Asp Gly Ser Asn Ser Ile Tyr Pro Trp Asp Ser Val Thr Ala Phe
            180                 185                 190

Leu Asn Asp Leu Leu Glu Arg Met Asp Ile Gly Pro Lys Gln Thr Gln
        195                 200                 205

Val Gly Ile Val Gln Tyr Gly Glu Asn Val Thr His Glu Phe Asn Leu
    210                 215                 220

Asn Lys Tyr Ser Ser Thr Glu Glu Val Leu Val Ala Ala Lys Lys Ile
225                 230                 235                 240

Val Gln Arg Gly Gly Arg Gln Thr Met Thr Ala Leu Gly Ile Asp Thr
                245                 250                 255

Ala Arg Lys Glu Ala Phe Thr Glu Ala Arg Gly Ala Arg Arg Gly Val
            260                 265                 270

Lys Lys Val Met Val Ile Val Thr Asp Gly Glu Ser His Asp Asn His
        275                 280                 285

Arg Leu Lys Lys Val Ile Gln Asp Cys Glu Asp Glu Asn Ile Gln Arg
    290                 295                 300

Phe Ser Ile Ala Ile Leu Gly Ser Tyr Asn Arg Gly Asn Leu Ser Thr
```

-continued

```
        305                 310                 315                 320
    Glu Lys Phe Val Glu Glu Ile Lys Ser Ile Ala Ser Glu Pro Thr Glu
                        325                 330                 335
    Lys His Phe Phe Asn Val Ser Asp Glu Leu Ala Leu Val Thr Ile Val
                        340                 345                 350
    Lys Thr Leu Gly Glu Arg Ile Phe Ala Leu Glu Ala Thr Ala Asp Gln
                        355                 360                 365
    Ser Ala Ala Ser Phe Glu Met Glu Met Ser Gln Thr Gly Phe Ser Ala
                        370                 375                 380
    His Tyr Ser Gln Asp Trp Val Met Leu Gly Ala Val Gly Ala Tyr Asp
    385                 390                 395                 400
    Trp Asn Gly Thr Val Val Met Gln Lys Ala Ser Gln Ile Ile Ile Pro
                        405                 410                 415
    Arg Asn Thr Thr Phe Asn Val Glu Ser Thr Lys Lys Asn Glu Pro Leu
                        420                 425                 430
    Ala Ser Tyr Leu Gly Tyr Thr Val Asn Ser Ala Thr Ala Ser Ser Gly
                        435                 440                 445
    Asp Val Leu Tyr Ile Ala Gly Gln Pro Arg Tyr Asn His Thr Gly Gln
                        450                 455                 460
    Val Ile Ile Tyr Arg Met Glu Asp Gly Asn Ile Lys Ile Leu Gln Thr
    465                 470                 475                 480
    Leu Ser Gly Glu Gln Ile Gly Ser Tyr Phe Gly Ser Ile Leu Thr Thr
                        485                 490                 495
    Thr Asp Ile Asp Lys Asp Ser Asn Thr Asp Ile Leu Leu Val Gly Ala
                        500                 505                 510
    Pro Met Tyr Met Gly Thr Glu Lys Glu Glu Gln Gly Lys Val Tyr Val
                        515                 520                 525
    Tyr Ala Leu Asn Gln Thr Arg Phe Glu Tyr Gln Met Ser Leu Glu Pro
                        530                 535                 540
    Ile Lys Gln Thr Cys Cys Ser Ser Arg Gln His Asn Ser Cys Thr Thr
    545                 550                 555                 560
    Glu Asn Lys Asn Glu Pro Cys Gly Ala Arg Phe Gly Thr Ala Ile Ala
                        565                 570                 575
    Ala Val Lys Asp Leu Asn Leu Asp Gly Phe Asn Asp Ile Val Ile Gly
                        580                 585                 590
    Ala Pro Leu Glu Asp Asp His Gly Gly Ala Val Tyr Ile Tyr His Gly
                        595                 600                 605
    Ser Gly Lys Thr Ile Arg Lys Glu Tyr Ala Gln Arg Ile Pro Ser Gly
                        610                 615                 620
    Gly Asp Gly Lys Thr Leu Lys Phe Phe Gly Gln Ser Ile His Gly Glu
    625                 630                 635                 640
    Met Asp Leu Asn Gly Asp Gly Leu Thr Asp Val Thr Ile Gly Gly Leu
                        645                 650                 655
    Gly Gly Ala Ala Leu Phe Trp Ser Arg Asp Val Ala Val Val Lys Val
                        660                 665                 670
    Thr Met Asn Phe Glu Pro Asn Lys Val Asn Ile Gln Lys Lys Asn Cys
                        675                 680                 685
    His Met Glu Gly Lys Glu Thr Val Cys Ile Asn Ala Thr Val Cys Phe
                        690                 695                 700
    Asp Val Lys Leu Lys Ser Lys Glu Asp Thr Ile Tyr Glu Ala Asp Leu
    705                 710                 715                 720
    Gln Tyr Arg Val Thr Leu Asp Ser Leu Arg Gln Ile Ser Arg Ser Phe
                        725                 730                 735
```

-continued

Phe Ser Gly Thr Gln Glu Arg Lys Val Gln Arg Asn Ile Thr Val Arg
              740                 745                 750

Lys Ser Glu Cys Thr Lys His Ser Phe Tyr Met Leu Asp Lys His Asp
              755                 760                 765

Phe Gln Asp Ser Val Arg Ile Thr Leu Asp Phe Asn Leu Thr Asp Pro
              770                 775                 780

Glu Asn Gly Pro Val Leu Asp Asp Ser Leu Pro Asn Ser Val His Glu
785                 790                 795                 800

Tyr Ile Pro Phe Ala Lys Asp Cys Gly Asn Lys Glu Lys Cys Ile Ser
              805                 810                 815

Asp Leu Ser Leu His Val Ala Thr Thr Glu Lys Asp Leu Leu Ile Val
              820                 825                 830

Arg Ser Gln Asn Asp Lys Phe Asn Val Ser Leu Thr Val Lys Asn Thr
              835                 840                 845

Lys Asp Ser Ala Tyr Asn Thr Arg Thr Ile Val His Tyr Ser Pro Asn
850                 855                 860

Leu Val Phe Ser Gly Ile Glu Ala Ile Gln Lys Asp Ser Cys Glu Ser
865                 870                 875                 880

Asn His Asn Ile Thr Cys Lys Val Gly Tyr Pro Phe Leu Arg Arg Gly
              885                 890                 895

Glu Met Val Thr Phe Lys Ile Leu Phe Gln Phe Asn Thr Ser Tyr Leu
              900                 905                 910

Met Glu Asn Val Thr Ile Tyr Leu Ser Ala Thr Ser Asp Ser Glu Glu
              915                 920                 925

Pro Pro Glu Thr Leu Ser Asp Asn Val Val Asn Ile Ser Ile Pro Val
              930                 935                 940

Lys Tyr Glu Val Gly Leu Gln Phe Tyr Ser Ser Ala Ser Glu Tyr His
945                 950                 955                 960

Ile Ser Ile Ala Ala Asn Glu Thr Val Pro Glu Val Ile Asn Ser Thr
              965                 970                 975

Glu Asp Ile Gly Asn Glu Ile Asn Ile Phe Tyr Leu Ile Arg Lys Ser
              980                 985                 990

Gly Ser Phe Pro Met Pro Glu Leu Lys Leu Ser Ile Ser Phe Pro Asn
              995                 1000                1005

Met Thr Ser Asn Gly Tyr Pro Val Leu Tyr Pro Thr Gly Leu Ser Ser
              1010                1015                1020

Ser Glu Asn Ala Asn Cys Arg Pro His Ile Phe Glu Asp Pro Phe Ser
1025                1030                1035                1040

Ile Asn Ser Gly Lys Lys Met Thr Thr Ser Thr Asp His Leu Lys Arg
              1045                1050                1055

Gly Thr Ile Leu Asp Cys Asn Thr Cys Lys Phe Ala Thr Ile Thr Cys
              1060                1065                1070

Asn Leu Thr Ser Ser Asp Ile Ser Gln Val Asn Val Ser Leu Ile Leu
              1075                1080                1085

Trp Lys Pro Thr Phe Ile Lys Ser Tyr Phe Ser Ser Leu Asn Leu Thr
              1090                1095                1100

Ile Arg Gly Glu Leu Arg Ser Glu Asn Ala Ser Leu Val Leu Ser Ser
1105                1110                1115                1120

Ser Asn Gln Lys Arg Glu Leu Ala Ile Gln Ile Ser Lys Asp Gly Leu
              1125                1130                1135

Pro Gly Arg Val Pro Leu Trp Val Ile Leu Leu Ser Ala Phe Ala Gly
              1140                1145                1150

Leu Leu Leu Leu Met Leu Leu Ile Leu Ala Leu Trp Lys Ile Gly Phe
            1155                1160                1165

Phe Lys Arg Pro Leu Lys Lys Lys Met Glu Lys
    1170                1175

<210> SEQ ID NO 2
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 3
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

METHODS FOR TREATMENT OR PREVENTION OF A NEUROLOGICAL IMMUNITY DISORDER

INCORPORATION BY REFERENCE OF PRIORITY APPLICATION

This Application is a 35 U.S.C. § 371 national stage filing of International Application No. PCT/US2018/042955, filed Jul. 19, 2018, which in turn claims the benefit of U.S. Provisional Application No. 62/534,895, filed Jul. 20, 2017, entitled "Methods for treatment or prevention of a neurological immunity disorder". The entire contents of each of the foregoing applications are incorporated by reference herein.

STATEMENT REGARDING FEDERALLY SPONSORED R&D

This invention was made with government support under Grant Nos. NS096967 and AG034113 awarded by the National Institutes of Health. The government has certain rights in the invention.

REFERENCE TO SEQUENCE LISTING

The present application is being filed along with a Sequence Listing in electronic format. The Sequence Listing is provided as a file entitled SEQ_LISTING_131819_00204.txt, created and last saved Aug. 13, 2021, which is 12,360 bytes in size. The information in the electronic format of the Sequence Listing is incorporated herein by reference in its entirety.

BACKGROUND

The central nervous system (CNS) and the immune system have very complex interactions that both control and modulate the function of each others[1-6]. Recent work emphasized the role of T cells in the regulation of cognition in mice[7-9]. Indeed, mice lacking a functional immune system, notably CD4 T cells, exhibit impaired performance of cognitive tasks. This impairment is rescued by injection of CD4 T cells back into immune deficient mice[7]. Under normal conditions, T cells are virtually absent from the brain parenchyma but are enriched in the surrounding of the brain called the meninges[5,8], notably around the major blood vessels in the dura mater, the sinuses[10]. It was previously unclear how T cells, localized in the meninges, are able to affect brain function.

Multiple sclerosis (MS) is characterized by the destruction of the CNS myelin and is considered to be an autoimmune disease. MS results in physical, mental, and/or psychiatric problems. Symptoms may include double vision, muscle weakness, trouble with sensation, or trouble with coordination. There is currently no cure for MS.

Alzheimer's disease (AD) is a type of dementia that is associated with memory loss, and problems with thinking and behavior. The parenchymal accumulation of neurotoxic amyloid beta (Aβ) is a central hallmark of AD. There is currently no cure for AD and treatments are limited to reducing and/or slowing the progression of the symptoms.

Autism spectrum disorder (ASD) is a neurodevelopmental disorder characterized by impaired social interaction, verbal and non-verbal communication, and restricted and repetitive behavior. There is currently no cure for ASD. There is a need in the field for methods of treatment for neurological immunity disorders, including but not limited to MS, AD and ASD. The present disclosure addresses this need.

FIELD

Embodiments herein relate to methods for treating, preventing, inhibiting or ameliorating a neurological immunity disorder, or a symptom thereof.

SUMMARY

In some embodiments, the present application provides methods of treating, preventing, inhibiting, delaying the onset of, or ameliorating a neurological immunity disorder or a symptom thereof in an animal subject. The method can comprise administering to the subject a therapeutically effective amount of a compound that inhibits (or blocks) integrin signaling. In some embodiments, methods of treating, preventing, inhibiting, delaying the onset of, or ameliorating a neurological immunity disorder or a symptom thereof in an animal subject are described. In some embodiments, the method comprises administering to the subject a therapeutically effective amount of a compound that decreases or inhibits CD49a function, for example by binding specifically to CD49a. In some embodiments, the method comprises administering to the subject a therapeutically effective amount of an antibody or antigen binding fragment which binds CD49a. In some embodiments, the compound that inhibits integrin signaling is administered after the onset of the neurological immunity disorder, for example at least about 8 days after the onset of the neurological immunity disorder, for example at least 5, 6, 7, 8, 9, 10, 11, 12, 13, 14, 15, 16, 17, 18, 19, 20, 21, 22, 23, 24, 25, 26, 27, or 28 days, including any range between any two of the listed values, for example, including but not limited to the following ranges which are provided for exemplary purposes only: 5-28 days, 5-21 days, 5-14 days, 5-7 days, 7-28 days, 7-21 days, 7-14 days, 10-28 days, 10-21 days, or 10-14 days. In some embodiments, the administration of the compound after the onset of the neurological immunity disorder reduces clinical symptoms of the neurological immunity disorder, which can be measured, for example, by a clinical score. In some embodiments, the compound that inhibits integrin signaling comprises, consists essentially of, or consists of a CD49a inhibiting (or blocking) antibody.

In some embodiments, the subject is a human. The compound can decrease CD49a function. In some embodiments, the compound comprises, consists of, or consists essentially of an antibody that binds specifically to CD49a, or an antigen binding fragment thereof. In some embodiments, the antibody or antigen binding fragment is a monoclonal antibody. In some embodiments, the antibody or antigen binding fragment is a human antibody. In some embodiments, the antibody or antigen binding fragment is a humanized antibody. In some embodiments, the antibody or antigen binding fragment is a chimeric antibody. In some embodiments, the compound that inhibits integrin signaling is an antibody or an antigen binding fragment which specifically binds CD49a. By "binds specifically to CD49a" it is understood that the antibody or antigen binding fragment binds preferentially to CD49a compared to other antigens, but there is no requirement that the antibody or antigen binding fragment bind with absolute specificity only to CD49a. In some embodiments, the antibody or antigen binding fragment binds specifically to CD49a compared to other integrins. In some embodiments, the antibody binds specifically to CD49a, and does not exhibit appreciable binding to any of CD49b, CD49c, CD49d, CD49e, and/or CD49f. Without being limited by theory, it is noted that CD49a-f represent the alpha 1 through 6 chains of beta 1 integrins, and as such, CD49a-f have different structures and CD49b-f are not expected to appreciably cross react with any antibody that binds specifically to CD49a. In some embodiments, the antibody does not bind specifically to any of CD49b, CD49c, CD49d, CD49e, and/or CD49f, including combinations of two or more of the listed molecules.

In some embodiments the method further comprises the step of identifying a subject in need of treatment. In certain embodiments the subject in need of treatment is susceptible to or suffering from a neurological immunity disorder selected from the group consisting of autism spectrum disorder (ASD), multiple sclerosis (MS), Alzheimer's disease (AD), and central nervous system (CNS) injury.

In some embodiments, administration of the compound (se.g., an antibody or antigen binding fragment specific for CD49a) is via intracerebroventricular injection. In other embodiments, an ointment comprises the compound and administration is via application of the ointment to the skin (scalp) of said subject. In some embodiments, the ointment comprises the compound and administration is via application of the ointment to the head of the subject, such as on the scalp.

In some embodiments, the administration of the compound (e.g., an antibody or antigen binding fragment specific for CD49a) results in accumulation of immune cells in the brain meninges. In particular embodiments, the administration of the compound results in elevated T cells and natural killer T (NKT) cells in the brain parenchyma.

In some embodiments, the present application provides a method of treating MS in a human subject, comprising administering to the subject a therapeutically effective amount of a CD49a inhibiting (or blocking) antibody or antigen binding fragment thereof. In particular embodiments, the method further comprises the step of identifying a subject in need of said treatment. In other embodiments, the administration of the CD49a inhibiting (or blocking) antibody is via intracerebroventricular injection. In still further embodiments, an ointment comprises said CD49a inhibiting (or blocking) antibody and the administration is via application of the ointment to the skin (scalp) of the subject. In some embodiments, an ointment comprises said CD49a inhibiting (or blocking) antibody and the administration is via application of the ointment to the head of the subject, such as on the scalp.

In some embodiments, the CD49a inhibiting (or blocking) antibody or antigen binding fragment thereof is administered after the onset of the neurological immunity disorder. In some embodiments, the administration of the CD49a inhibiting (or blocking) antibody or antigen binding fragment thereof after the onset of the neurological immunity disorder reduces clinical symptoms of the neurological immunity disorder, which can be measure, for example, by a clinical score.

BRIEF DESCRIPTION OF THE DRAWINGS

FIGS. 1A-1F show the presence of two main distinct populations of T cells in meninges of naïve mice. FIG. 1A is a representative contour plot of the CD4 T cell populations in the diaphragm and meninges of naïve mice. FIG. 1B is a quantification of the percentage of $CD44^{High}CD69^+$, $CD44^{High}CD69^-$ and $CD44^-CD69^-$ T cells in the diaphragm and meninges of naïve mice. Contrary to the diaphragm, the meninges have two major populations of T cells that can be discriminated by the expression of CD69. FIG. 1C is a representative histogram and quantification of CD11a expression by the meningeal T cell populations. FIG. 1D is a representative histogram and quantification of CD103 expression by meningeal T cell populations. FIG. 1E is a representative histogram and quantification of CD49a expression by meningeal T cell populations. FIG. 1F is a representative histogram and quantification of CD49s expression by meningeal T cell populations. Mean+/−SEM, N=3 mice per group. ***p<0.001, One-way ANOVA with Bonferroni post test. The CD69+ CD4 T cell population also expresses high levels of CD49a and CD11a.

FIGS. 2A-2J show that blockade of CD49a induces the transient accumulation of immune cells in the meninges. FIG. 2A is a representative histogram of CD49a expression by the different meningeal immune cell populations. FIG. 2B is a quantification of the percentage of CD49a expressing cells within the different immune cell populations in naïve meninges. CD49a is not only expressed by the meningeal T cells but also by several other immune cells like monocytes/macrophages, NK, and NKT cells. FIG. 2C is a set of representative dot plots of T cells, NK, and NKT cells in the meninges of mice after IgG or CD49a blocking antibody injection. FIG. 2D is a quantification of the number of different immune cell populations in the meninges after IgG or CD49a blocking antibody injection. FIG. 2E is a set of representative images of CD3, CD4, and CD45 immunostaining in the meninges of mice after IgG or CD49a blocking antibody injection. The CD49a-injected mice exhibited higher levels of CD3e, CD4, and CD45 staining compared to the IgG-injected mice. FIGS. 2F-G is a quantification of the density of $CD3^+$ T cells (FIG. 2F) and coverage of $CD45^+$ cells (FIG. 2G) in the different regions of the meninges after IgG or CD49a treatment. FIG. 2H is a set of representative dot plots of BrdU incorporation in the CD4 T cells of the meninges after IgG or CD49a blocking antibody injection. The CD49a-injected mice exhibited higher levels of BrdU staining than the CD4 controls. FIG. 2I is a quantification of the percentage of BrdU+ CD4 T cells in the meninges of IgG and CD49a treated mice. FIG. 2J is a quantification of the number of CD4 effector T cells ($TCRb^+$ $CD4^+NK1.1^-FoxP3^-$) in the meninges of IgG and CD49a treated mice at different days post injection. Mean+/−SEM, N=3-4 mice per group. *p<0.05, p<0.01, *p<0.001, One way ANOVA or Two way ANOVA with Bonferoni post test.

FIG. 3A is a series of representative images of brain sections of IgG and CD49a treated mice immunostained for immune infiltrate (CD45—red) and astrocytes end feet (AQP4—green). Greater levels of CD45 staining (infiltrating immune cells) were observed in the brain parenchyma CD49a-treated mice compared to the IgG-treated control mice at 48 hours, and even greater levels of CD45 staining were observed in the CD49a-treated mice at 72 hours. FIG. 3B is a quantification of the density of CD45+ cells in the brain parenchyma of IgG and CD49a treated mice at different time post injection. FIG. 3C is a set of representative dot plots of $CD45^{High}$ and $CD45^{Low}$ expressing cells in the cortex and cerebellum after IgG and anti-CD49a treated mice. Greater proportions of cerebellum and cortex/hippocampus cells were CD45-high in the anti-CD49a-treated mice compared to IgG-treated controls. FIG. 3D is a quantification of the number of $CD45^{High}$ and $CD45^{Low}$ cells in the cortex/hippocampus and cerebellum of mice after IgG and CD49a blockade. FIG. 3E is a graph depicting gating of the phenotype of CD45$^{High}$ cells in the brain of CD49a treated mice. Mean+/−SEM, N=3-4 mice per group. *p<0.05; **p<0.01, One way ANOVA with Bonferoni post test.

FIGS. 4A-4E show that infiltration of cells is not due to blood brain barrier opening but rather trans-pial migration. FIG. 4A is a set of representative images of hemi-brain of IgG and anti-CD49a injected mice after i.v. Evans Blue injection. FIG. 4B is a quantification of the Evans Blue concentration in the brain of IgG and anti-CD49a injected mice. FIG. 4C is a set of representative images of meninges of IgG and anti-CD49a injected mice after i.v. Evans Blue injection. FIG. 4D is a diagram of the scheme of the photoconversion of meningeal KiKGR expressing cells. FIG. 4E is a representative dot plot of green (non photoconverted) and red (photoconverted) CD45High cells in the cortex of anti-CD49a treated mice, 24 h after injection.

FIG. 7A shows quantification of the number of CD45+, T cells, and NK cells in the meninges of sham or denervated IgG and CD49a treated mice. (mean±s.e.m.; n=5 mice/group, *p<0.001, two-way ANOVA). FIG. 7B shows quantification of geometric mean fluorescence intensity for ICAM1, VCAM1 and CD49a by the meningeal endothelial cells of sham or denervated IgG and CD49a treated mice. (mean±s.e.m.; n=5 mice/group, *p<0.001, two-way ANOVA).

FIG. 8A shows quantification of the CD45 coverage in the SSS of mice. (mean±s.e.m.; n=4/5 mice/group). FIG. 8B shows quantification of the MHCII coverage in the SSS of mice. (mean±s.e.m.; n=4/5 mice/group). FIG. 8C shows quantification of the CD3e coverage in the SSS of mice. (mean±s.e.m.; n=4/5 mice/group). FIG. 8G shows quantification of the density of CD3e cells in the SSS of mice. (mean±s.e.m.; n=4/5 mice/group).

FIG. 9A shows clinical score of IgG and CD49a treated mice. (mean±s.e.m.; n=36/37 mice/group; p<0.01; repeated measures two-way ANOVA). FIG. 9B shows incidence of clinical symptoms development of IgG and CD49a treated mice. (mean±s.e.m.; n=36/37 mice/group; *p<0.001; Log-rank test). FIG. 9C shows clinical score score of symptomatic IgG and CD49a treated mice (mean±s.e.m.; n=24/35 mice/group).

FIG. 9D shows quantification of the CD45 coverage, CD45+ cells density and density of CD45 cluster in the cerebellum and cortex of IgG and CD49a treated mice induced with EAE. (mean±s.e.m.; n=3/10 mice/group) FIG. 9E shows quantification of the CD45 coverage in the spinal cord of IgG and CD49a treated mice induced with EAE. (mean±s.e.m.; n=4/9 mice/group)

DETAILED DESCRIPTION

Figures 1A, 1B:
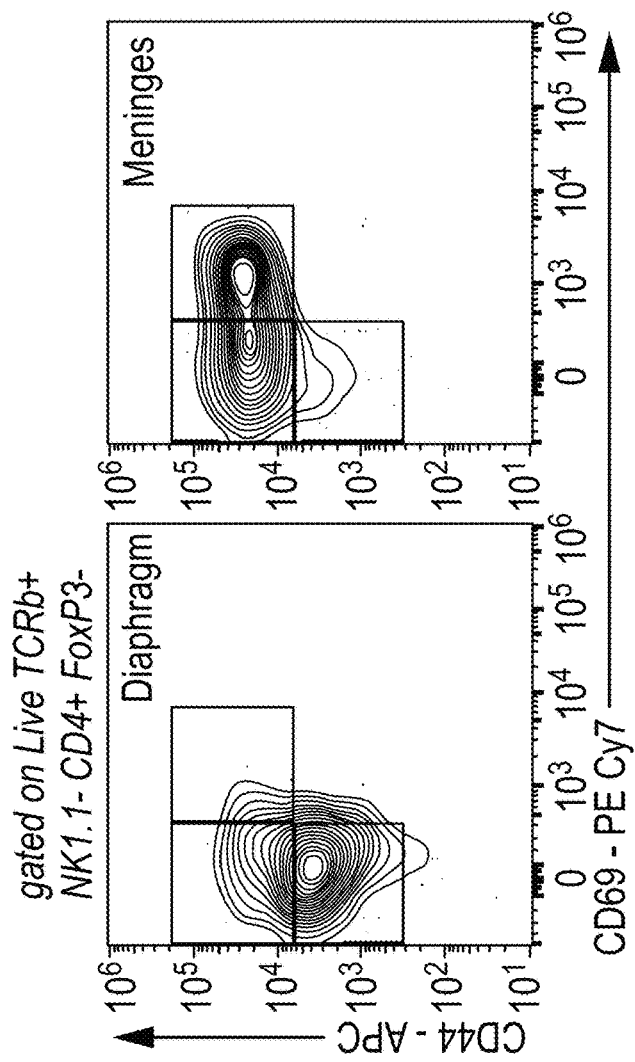

Some embodiments provide methods of treating or preventing a neurological immunity disorder in an animal subject, comprising administering to the subject a therapeutically effective amount of a compound that inhibits integrin signaling. Some embodiments provide methods of treating or preventing a neurological immunity disorder in an animal subject, comprising administering to the subject a therapeutically effective amount of a compound that decreases CD49a function. Some embodiments provide method of treating a neurological immunity disorder in an animal subject, comprising administering to the subject a therapeutically effective amount of an antibody or antigen binding fragment which binds CD49a, for example a human or humanized antibody or antigen binding fragment thereof that binds specifically to CD49a. In some embodiments, the antibody or antigen binding fragment thereof does not bind specifically to any of CD49b, CD49c, CD49d, CD49e, and/or CD49f, including combinations of two or more of these. In some embodiments, the compound blocks integrin signaling. It is noted that wherever a method of treating a disease or disorder with a composition is described herein, the corresponding use of the composition for the treatment of the disease or disorder is also expressly contemplated. For example, wherever a method of treating a neurological immunity disorder with an antibody or antigen binding fragment that binds to CD49a is described herein, an antibody or antigen binding fragment that binds to CD49a for use in treating the neurological immunity disorder is also expressly contemplated. It is to be understood that the embodiments described herein are not limited to specific analytical or synthetic methods as such may, of course, vary. It is also to be understood that the terminology used herein is for the purpose of describing particular embodiments only and is not intended to be limiting. Unless defined otherwise, all technical and scientific terms used herein have the meaning commonly understood by one of ordinary skill in the art to which this disclosure belongs, in view of the present disclosure.

"Neurological immunity disorders" is used herein according to its customary and ordinary meaning as would be understood by one of ordinary skill in the art in view of the specification, and encompasses neurological disorders with an immune component, for example, MS, Central Nervous System (CNS) injury, AD, and ASD.

The terms "treatment," "treating," and the like have their customary and ordinary meaning as understood by one of skill in the art in view of this disclosure. They generally refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein has is customary and ordinary meaning as understood by one of skill in the art in view of this disclosure, and encompasses any treatment of a disease or symptom in a mammal, and includes any one or more of the following: (a) preventing the disease or a symptom from occurring in a subject which may be predisposed to acquiring the disease or symptom but has not yet been diagnosed as having it; (b) inhibiting the disease or a symptom, e.g., arresting or slowing its development; (c) relieving the disease, e.g., causing regression of the disease; (d) ameliorating one or more symptoms of the disease; (e) delaying the onset of the disease; and (e) reducing the likelihood of occurrence of the disease. The therapeutic agent (such as an anti-CD49a antibody or binding fragment thereof) may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

As used herein, the term "integrin" has its customary and ordinary meaning as understood by one of skill in the art in view of this disclosure. It refers to proteins that are transmembrane receptors that function to facilitate cell-cell and cell-extracellular matrix interactions. Examples of integrins and integrin subunits expressed in the meninges include CD49a, LFA1, itga11, CD49e, itga8, CD51, CD49f, and itga9.

As used herein, the singular forms "a," "an," and "the" include plural reference unless the context clearly dictates otherwise. Thus, for example, reference to "a reagent" is reference to one or more reagents and includes equivalents thereof known to those skilled in the art. Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "about" is used herein to provide literal support for the exact number that it precedes, as well as a number that differs from the given number without having a substantial effect in the context. If more numerical precision is desired, "about" refers to values that differ by less than ±10%. In some embodiments, the term "about" indicates that the number differs from the given number by less than ±9%, 8%, 7%, 6%, 5%, 4%, 3%, 2%, or 1%.

It is appreciated that certain features described herein, which are, for clarity, described separately and/or in the context of separate embodiments, may also be provided in combination in a single embodiment. Conversely, various features of embodiments herein, which are, for brevity, described in the context of a single embodiment, may also be provided separately or in any suitable sub-combination. All combinations of the embodiments described herein are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

In some embodiments, a method of treating, preventing, inhibiting, reducing the likelihood of, and/or delaying the onset of a neurological immunity disorder in an animal subject is described. The method can comprise administering to the subject a therapeutically effective amount of a compound that inhibits integrin signaling. The compound can comprise, consist essentially of, or consist of an inhibitor of CD49a, for example an antibody or antigen binding fragment thereof that binds specifically to CD49a. In some embodiments, the antibody or antigen binding fragment thereof that binds specifically to CD49a is a monoclonal antibody. In some embodiments, the neurological immunity disorder is selected from the group autism spectrum disorder (ASD), multiple sclerosis (MS), Alzheimer's disease (AD), and central nervous system (CNS) injury. In some embodiments, the method comprises treating or preventing the neurological immunity disorder, for example, ASD, MS, AD, and/or CNS. In some embodiments, the animal subject is a human. In some embodiments, the compound is formulated for administration to the CNS of the subject, for example intracerebroventricular administration. In some embodiments, the compound is administered to the CNS of the subject, for example intracerebroventricular administration. In some embodiments, the compound is not administered outside the CNS.

In some embodiments, the method treats prevents, inhibits, reduces the likelihood of, and/or delays the onset of a neurological immunity disorder in a human subject. In some embodiments, the method comprises administering to the subject a therapeutically effective amount of a compound that inhibits CD49a signaling. In some embodiments, the compound comprises, consists essentially of, or consists of an antibody or antigen binding fragment thereof that binds specifically to CD49a. In some embodiments, the compound comprises, consists essentially of, or consists of a monoclonal antibody or antigen binding fragment thereof that binds specifically to CD49a. In some embodiments, the neurological immunity disorder is selected from the group consisting of ASD, MS, AD, and CNS injury. In some embodiments, the method comprises treating or preventing the neurological immunity disorder. In some embodiments, the compound is formulated for administration to the CNS of the subject, for example intracerebroventricular administration. In some embodiments, the compound is administered to the CNS of the subject, for example intracerebroventricular administration. In some embodiments, the compound is not administered outside the CNS.

In some embodiments, the method treats, prevents, inhibits, reduces the likelihood of, and/or delays the onset of ASD in a human subject. In some embodiments, the method comprises administering to the subject a therapeutically effective amount of a compound that inhibits CD49a signaling. In some embodiments, the compound comprises, consists essentially of, or consists of an antibody or antigen binding fragment thereof that binds specifically to CD49a. In some embodiments, the compound comprises, consists essentially of, or consists of a monoclonal antibody or antigen binding fragment thereof that binds specifically to CD49a. In some embodiments, the antibody, e.g., monoclonal antibody or antigen binding fragment thereof does not specifically bind to any of CD49b, CD49c, CD49d, Cd49e, and/or CD49f. In some embodiments, the method comprises treating or preventing the ASD. In some embodiments, the compound is formulated for administration to the CNS of the subject, for example intracerebroventricular administration. In some embodiments, the compound is administered to the CNS of the subject, for example intracerebroventricular administration. In some embodiments, the compound is not administered outside the CNS.

In some embodiments, the method treats, prevents, inhibits, reduces the likelihood of, and/or delays the onset of MS in a human subject. In some embodiments, the method comprises administering to the subject a therapeutically effective amount of a compound that inhibits CD49a signaling. In some embodiments, the compound comprises, consists essentially of, or consists of an antibody or antigen binding fragment thereof that binds specifically to CD49a. In some embodiments, the compound comprises, consists essentially of, or consists of a monoclonal antibody or antigen binding fragment thereof that binds specifically to CD49a. In some embodiments, the antibody, e.g., monoclonal antibody or antigen binding fragment thereof does not bind to any of CD49b, CD49c, CD49d, Cd49e, and/or CD49f. In some embodiments, the method comprises treating or preventing the MS. As shown in Example 4, 5, and 7 and FIGS. 5, 6A-B, and 9A-C, administering an antibody inhibitor of CD49a signaling to an EAE subject (a model of MS) in accordance with some embodiments herein delayed the onset of EAE, reduced the incidence of EAE, and improved the clinical score of the EAE subject. Accordingly, it is contemplated that administering an inhibitor of CD49a (such as an antibody or antigen binding fragment thereof that binds specifically to CD49a) in accordance with some embodiments herein can delay the onset of, reduce the incidence of, and/or ameliorate symptoms of MS. In some embodiments, the compound is formulated for administration to the CNS of the subject, for example intracerebroventricular administration. In some embodiments, the compound is administered to the CNS of the subject, for example intracerebroventricular administration. In some embodiments, the compound is not administered outside the CNS.

In some embodiments, the method treats, prevents, inhibits, reduces the likelihood of, and/or delays the onset of AD in a human subject. The method can comprise administering to the subject a therapeutically effective amount of a compound that inhibits CD49a signaling. The compound can comprise, consist essentially of, or consist of an antibody or antigen binding fragment thereof that binds specifically to CD49a. In some embodiments, the compound comprises, consists essentially of, or consists of a monoclonal antibody or antigen binding fragment thereof that binds specifically to CD49a. In some embodiments, the antibody, e.g., monoclonal antibody or antigen binding fragment thereof does not bind to any of CD49b, CD49c, CD49d, Cd49e, and/or CD49f. In some embodiments, the method comprises treating or preventing the AD. In some embodiments, the compound is formulated for administration to the CNS of the subject, for example intracerebroventricular administration. In some embodiments, the compound is administered to the CNS of the subject, for example intracerebroventricular administration. In some embodiments, the compound is not administered outside the CNS.

In some embodiments, the method treats, prevents, inhibits, and/or delays the onset of CNS injury in a human subject. The method can comprise administering to the subject a therapeutically effective amount of a compound that inhibits CD49a signaling. The compound can comprise, consist essentially of, or consist of an antibody or antigen binding fragment thereof that binds specifically to CD49a. In some embodiments, the compound comprises, consists essentially of, or consists of a monoclonal antibody or antigen binding fragment thereof that binds specifically to CD49a. In some embodiments, the antibody, e.g., monoclonal antibody or antigen binding fragment thereof does not bind to any of CD49b, CD49c, CD49d, Cd49e, and/or CD49f. In some embodiments, the method comprises treating or preventing the CNS injury. In some embodiments, the compound is formulated for administration to the CNS of the subject, for example intracerebroventricular administration. In some embodiments, the compound is administered to the CNS of the subject, for example intracerebroventricular administration. In some embodiments, the compound is not administered outside the CNS.

In the method or use of some embodiments, the compound that inhibits integrin signaling is administered after the onset of the neurological immunity disorder, for example at least about 8 days after the onset of the neurological immunity disorder, for example at least 5, 6, 7, 8, 9, 10, 11, 12, 13, 14, 15, 16, 17, 18, 19, 20, 21, 22, 23, 24, 25, 26, 27, or 28 days, including any ranges between any two of the listed values, for example, including but not limited to the following ranges which are provided for exemplary purposes only: 5-28 days, 5-21 days, 5-14 days, 5-7 days, 7-28 days, 7-21 days, 7-14 days, 10-28 days, 10-21 days, or 10-14 days. In the method or use of some embodiments, the administration of the compound after the onset of the neurological immunity disorder reduces clinical symptoms of the neurological immunity disorder, which can be measured, for example, by a clinical score. In the method or use of some embodiments, the compound that inhibits integrin signaling comprises, consists essentially of, or consists of an antibody or antigen binding fragment thereof that binds specifically to CD49a. In the method or use of some embodiments, the compound that inhibits integrin signaling comprises, consists essentially of, or consists of a CD49a inhibiting (or blocking) antibody.

In the method or use of some embodiments, the method further comprises identifying a subject in need of said treatment. In further embodiments, the subject in need of said treatment is susceptible to or suffering form a neurological immunity disorder selected from the group consisting of autism spectrum disorder (ASD), multiple sclerosis (MS), Alzheimer's disease (AD), and central nervous system (CNS) injury. Identification of such subjects may be made using techniques known to a person of ordinary skill in the art.

The term "subject" is used herein according to its customary and ordinary meaning as would be understood by one of ordinary skill in the art in view of the specification. It refers to an animal, for example a mammal, such as a human. In the method or use of some embodiments, the animal subject is a human.

In the method or use of some embodiments, inhibiting (or blocking) integrin signaling includes decreasing function of an integrin and/or decreasing function of an integrin subunit such as CD49a. In the method or use of some embodiments, the compound that inhibits integrin signaling decreases the function of a protein selected from the list consisting of CD49a, LFA1, itga11, CD49e, itga8, CD51, CD49f, and itga9. In the method or use of some embodiments, the compound that inhibits integrin signaling decreases CD49a function. In the method or use of some embodiments, the compound binds specifically to CD49a.

In the method or use of some embodiments, the compound that inhibits integrin signaling is an antibody or an antigen binding fragment which binds to an integrin or an integrin subunit. In some embodiments, the antibody or the antigen binding fragment binds a protein selected from the list consisting of CD49a, LFA1, itga11, CD49e, itga8, CD51, CD49f, and itga9. In some embodiments, the antibody or the antigen binding fragment binds to CD49a. In some embodiments, the antibody or the antigen binding fragment specifically binds a protein selected from the list consisting of CD49a, LFA1, itga11, CD49e, itga8, CD51, CD49f, and itga9. In some embodiments, the antibody or the antigen binding fragment specifically binds CD49a. In some embodiments, the antibody or the antigen binding fragments is a monoclonal antibody, for example a humanized antibody or human antibody.

An antibody (interchangeably used in plural form) is used herein according to its customary and ordinary meaning as would be understood by one of ordinary skill in the art in view of the specification. It refers to an immunoglobulin molecule capable of specific binding to a target, such as a carbohydrate, polynucleotide, lipid, polypeptide, etc., through at least one antigen recognition site, which is typically located in the variable region of the immunoglobulin molecule. As used herein, the term "antibody", e.g., anti-CD49a antibody, encompasses not only intact (e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody, e.g., anti-CD49a antibody in accordance with methods, uses, compositions, and pharmaceutical compositions of some embodiments herein, includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The base structure of an antibody is a tetramer, which includes two heavy chains and two light chains. Each chain comprises a constant region, and a variable region. Generally, the variable region, heavy chain variable region ($V_H$) and a light chain variable region ($V_L$), is responsible for binding specificity of the antibody. In a typical antibody, each variable region comprises three complementarity determining regions (CDRs) flanked by four framework (FR) regions. As such, an typical antibody variable region has six CDRs (three heavy chain CDRs, three light chain CDRs), some or all of which are generally involved in binding interactions by the antibody. Each $V_H$ and $V_L$ comprises three CDRs and four FRs, arranged from amino-terminus to carboxy-terminus in the following order: FR1, CDR1, FR2, CDR2, FR3, CDR3, FR4. The framework regions and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs).

The anti-CD49a antibody suitable for methods, uses, compositions, and pharmaceutical compositions of embodiments described herein may be a full-length antibody, which contains two heavy chains and two light chains, each including a variable domain and a constant domain. Alternatively, the anti-CD49a antibody can be an antigen-binding fragment of a full-length antibody. Examples of binding fragments encompassed within the term "antigen-binding fragment" of a full length antibody include (i) a Fab fragment, a monovalent fragment consisting of the $V_L$, $V_H$, $C_L$ and $C_H1$ domains; (ii) a F(ab')2 fragment, a bivalent fragment including two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) that retains functionality. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

Anti-CD49a antibodies and methods for producing them are known in the art. For example, US20160017043 provides antibody sequences for anti-CD49a antibodies, which publication is incorporated by reference in its entirety herein, including the drawings and the sequence listing therein. In some embodiments, the anti-CD49a antibody comprises a $V_L$ domain of the $V_L$ domain shown in FIG. 2A of US20160017043 and a $V_H$ domain of the $V_H$ domain shown in FIG. 2B of US20160017043. In some embodiments, the anti-CD49a antibody comprises a $V_L$ domain comprising a light chain CDR1, CDR2, and CDR3 that are light chain CDRs in the sequence shown in FIG. 2A of US20160017043 and a $V_H$ domain comprising a heavy chain CDR1, CDR2, and CDR3 that are heavy chain CDRs the sequence shown in FIG. 2B of US20160017043. In some embodiments, the anti-CD49a antibody comprises a $V_L$ domain of the $V_L$ domain shown in FIG. 3 of US20160017043 and a $V_H$ domain of the $V_H$ domain shown in FIG. 4 of US20160017043. In some embodiments, the anti-CD49a antibody comprises a $V_L$ domain comprising a light chain CDR1, CDR2, and CDR3 that are light chain CDRs in the sequence shown in FIG. 3 of US20160017043 and a $V_H$ domain comprising a heavy chain CDR1, CDR2, and CDR3 that are heavy chain CDRs in the sequence shown in FIG. 4 of US20160017043. In some embodiments, the CDRs are according to the definition of Kabat, Chothia, the Abm, or the contact definition. In some embodiments the anti-CD49a antibody is a human or humanized antibody as described herein.

In some embodiments, the anti-CD49a antibody comprises a $V_L$ domain that has at least 80%, at least 85%, at least 90% (e.g., 91%, 92%, 93%, 94%), at least 95% (e.g., 96%, 97%, 98%, 99%, 100%) sequence identity with the $V_L$ domain shown in FIG. 2A of US20160017043 and a $V_H$ domain that has at least 80%, at least 85%, at least 90% (e.g., 91%, 92%, 93%, 94%), at least 95% (e.g., 96%, 97%, 98%, 99%, 100%) sequence identity with the $V_H$ domain shown in FIG. 2B of US20160017043. In some embodiments, the anti-CD49a antibody comprises a $V_L$ domain having a sequence that differs from the $V_L$ domain shown in FIG. 2A of US20160017043 by 1, 2, 3, 4, 5, 6, 7, 9, or 10 amino acid residues and a $V_H$ domain having a sequence that differs from the $V_H$ domain shown in FIG. 2B of US20160017043 by 1, 2, 3, 4, 5, 6, 7, 9, or 10 amino acid residues. In some embodiments, the anti-CD49a antibody comprises a $V_L$ domain having a sequence that differs from the $V_L$ domain shown in FIG. 2A of US20160017043 by 1, 2, 3, 4, 5, 6, 7, 9, or 10 amino acid residues and a $V_H$ domain having a sequence of the $V_H$ domain shown in FIG. 2B of US2016001704. In some embodiments, the anti-CD49a antibody comprises a $V_L$ domain having a sequence of the $V_L$ domain shown in FIG. 2A of US20160017043, and a $V_H$ domain having a sequence that differs from the $V_H$ domain shown in FIG. 2B of US20160017043 by 1, 2, 3, 4, 5, 6, 7, 9, or 10 amino acid residues. In some embodiments, the anti-CD49a antibody comprises a $V_L$ domain comprising a light chain CDR1, CDR2, and CDR3 that are light chain CDRs having at least 80%, at least 85%, at least 90% (e.g., 91%, 92%, 93%, 94%), at least 95% (e.g., 96%, 97%, 98%, 99%, 100%) sequence identity with the light chain CDRs of the sequence shown in FIG. 2A of US20160017043 and a $V_H$ domain comprising a heavy chain CDR1, CDR2, and CDR3 that are heavy chain CDRs having at least 80%, at least 85%, at least 90% (e.g., 91%, 92%, 93%, 94%), at least 95% (e.g., 96%, 97%, 98%, 99%, 100%) sequence identity with the heavy chain CDRs of the sequence shown in FIG. 2B of US20160017043. In some embodiments, the anti-CD49a antibody comprises a $V_L$ domain comprising a light chain CDR1, CDR2, and CDR3 that are light chain CDRs having a sequence that differs from the sequence of the light chain CDRs shown in FIG. 2A of US20160017043 by 0, 1, 2, 3, 4, 5, 6, 7, 9, or 10 amino acid residues and a $V_H$ domain comprising a heavy chain CDR1, CDR2, and CDR3 that are heavy chain CDRs having a sequence that differs from the sequence of the heavy chain CDRs shown in FIG. 2B of US20160017043 by 0, 1, 2, 3, 4, 5, 6, 7, 9, or 10 amino acid residues. In some embodiments, the anti-CD49a antibody comprises a $V_L$ domain having at least 80%, at least 85%, at least 90% (e.g., 91%, 92%, 93%, 94%), at least 95% (e.g., 96%, 97%, 98%, 99%, 100%) sequence identity with the $V_L$ domain shown in FIG. 3 of US20160017043 and a $V_H$ domain having at least 80%, at least 85%, at least 90% (e.g., 91%, 92%, 93%, 94%), at least 95% (e.g., 96%, 97%, 98%, 99%, 100%) sequence identity with the $V_H$ domain shown in FIG. 4 of US20160017043. In some embodiments, the anti-CD49a antibody comprises a $V_L$ domain having a sequence that differs from the $V_L$ domain shown in FIG. 3 of US20160017043 by 1, 2, 3, 4, 5, 6, 7, 9 or 10 amino acid residues and a $V_H$ domain having a sequence that differs from the $V_H$ domain shown in FIG. 4 of US20160017043 by 1, 2, 3, 4, 5, 6, 7, 9, or 10 amino acid residues. In some embodiments, the anti-CD49a antibody comprises a $V_L$ domain having a sequence of the $V_L$ domain shown in FIG. 3 of US20160017043 and a $V_H$ domain having a sequence that differs from the $V_H$ domain shown in FIG. 4 of US20160017043 by 1, 2, 3, 4, 5, 6, 7, 9 or 10 amino acid residues. In some embodiments, the anti-CD49a antibody comprises a $V_L$ domain having a sequence that differs from the $V_L$ domain shown in FIG. 3 of US20160017043 by 1, 2, 3, 4, 5, 6, 7, 9 or 10 amino acid residues and a $V_H$ domain of the $V_H$ domain shown in FIG. 4 of US20160017043. In some embodiments, the anti-CD49a antibody comprises a $V_L$ domain comprising a light chain CDR1, CDR2, and CDR3 that are light chain CDRs having at least 80%, at least 85%, at least 90% (e.g., 91%, 92%, 93%, 94%), at least 95% (e.g., 96%, 97%, 98%, 99%, 100%) sequence identity with the sequence shown in FIG. 3 of US20160017043 and a $V_H$ domain comprising a heavy chain CDR1, CDR2, and CDR3 that are heavy chain CDRs having at least 80%, at least 85%, at least 90% (e.g., 91%, 92%, 93%, 94%), at least 95% (e.g., 96%, 97%, 98%, 99%, 100%) sequence identity with the heavy chain CDR sequences shown in FIG. 4 of US20160017043. In some embodiments, the anti-CD49a antibody comprises a $V_L$ domain comprising a light chain CDR1, CDR2, and CDR3 that are light chain CDRs having a sequence that differs from the light chain CDR sequences shown in FIG. 3 of US20160017043 by L 2, 3, 4, 5, 6, 7, 9, or 10 amino acid residues and a $V_H$ domain comprising a heavy chain CDR1, CDR2, and CDR3 that are heavy chain CDRs having a sequence that differs from the heavy chain CDR sequences shown in FIG. 4 of US20160017043 by 1, 2, 3, 4, 5, 6, 7, 9, or 10 amino acid residues.

In some embodiments, the anti-CD49a antibody comprises a VL domain of SEQ ID NO: 2 and a VH domain of SEQ ID NO: 3. In some embodiments, the anti-CD49a antibody comprises a VL domain that has at least 80%, at least 85%, at least 90% (e.g., 91%, 92%, 93%, 94%), at least 95% (e.g., 96%, 97%, 98%, 99%, 100%) sequence identity SEQ ID NO: 2 and a VH domain that has at least 80%, at least 85%, at least 90% (e.g., 91%, 92%, 93%, 94%), at least 95% (e.g., 96%, 97%, 98%, 99%, 100%) sequence identity with SEQ ID NO:3. In some embodiments, the anti-CD49a antibody comprises a VL domain having a sequence that differs from SEQ ID NO: 2 by 1, 2, 3, 4, 5, 6, 7, 9, or 10 amino acid residues and a VH domain having a sequence that differs from SEQ ID NO: 3 by 1, 2, 3, 4, 5, 6, 7, 9, or 10 amino acid residues.

Gln Ile Gln Leu Thr Gln Ser Pro Ser Ser Leu Ser Ala Ser Val Gly Asp Arg Val Thr Ile Thr Cys Ser Ala Ser Ser Ser Val Asn His Met Phe Trp Tyr Gln Gln Lys Pro Gly Lys Ala Pro Lys Pro Trp Ile Tyr Leu Thr Ser Asn Leu Ala Ser Gly Val Pro Ser Arg Phe Ser Gly Ser Gly Ser Gly Thr Asp Tyr Thr Leu Thr Ile Ser Ser Leu Gln Pro Glu Asp Phe Ala Thr Tyr Tyr Cys Gln Gln Trp Ser Gly Asn Pro Trp Thr Phe Gly Gln Gly Thr Lys Val Glu Ile Lys (SEQ ID NO: 2)

Glu Val Gln Leu Val Glu Ser Gly Gly Gly Leu Val Gln Pro Gly Gly Ser Leu Arg Leu Ser Cys Ala Ala Ser Gly Phe Thr Phe Ser Arg Tyr Thr Met Ser Trp Val Arg Gln Ala Pro Gly Lys Gly Leu Glu Trp Val Ala Thr Ile Ser Gly Gly Gly His Thr Tyr Tyr Leu Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Thr Arg Gly Phe Gly Asp Gly Gly Tyr Phe Asp Val Trp Gly Gln Gly Thr Leu Val Thr Val Ser Ser (SEQ ID NO: 3)

A number of approaches are available for producing suitable antibodies that specifically bind to CD49a in accordance with methods, uses, compositions, and pharmaceutical compositions of embodiments herein. For example, in some embodiments, a host organism is immunized with an antigen comprising, consisting essentially of, or consisting of CD49a. By way of example, a sequence of CD49a (which may also be referred to as Integrin alpha-1 or VLA-1) is available as Uniprot accession no. P56199 (SEQ ID NO: 1 MAPRPRARPGVAVACCWLLTVVLRCCVSFNVDV KNSMTFSGPVEDMFGYTVQQYE NEEGKWVLIGSPLVGQPKNRTGDVYKCPVGRGESLP CVKLDLPVNTSIPNVTEVKEN MTFGSTLVTNPNGG-FLACGPLYAYRCGHLHYTTGICSDVSPTFQVVNSI- APVQECST QLDIVIVLDGSNSIYPWDSVTAFLNDLLERM-DIGPKQTQVGIVQYGENVTHEFNLNKY SSTEEVLVAAKKIVQRGGRQTMTALGIDTARKEAF-TEARGARRGVKKVMVIVTDGE SHDNHRLKKVIQDCEDENIQRFSIAILGSYNRGNL-STEKFVEEIKSIASEPTEKHFFNVS DELALV-TIVKTLGERIFALEATADQSAASFEMEMSQTGF-SAHYSQDWVMLGAVGAY DWNGTVVMQKASQIIIPRNTTFNVESTKKNEPLA-SYLGYTVNSATASSGDVLYIAGQ PRYNHTGQVIIYRMEDGNIKILQTLSGEQI-GSYFGSILTTTDIDKDSNTDILLVGAPMY MGTEKE-EQGKVYVYALNQTRFEYQMSLEPIKQTCCSSRQHN-SCTTENKNEPCGARF GTAIAAVKDLNLDGFNDIVIGAPLEDDHG-GAVYIYHGSGKTIRKEYAQRIPSGGDGKT LKFFGQSIHGEMDLNGDGLTDVTIGGLG-GAALFWSRDVAVVKVTMNFEPNKVNIQK KNCH-MEGKETVCINATVCFDVKLKSKEDTI-YEADLQYRVTLDSLRQISRSFFSGTQER KVQRNITVRK-SECTKHSFYMLDKHDFQDSVRITLDFNLTDPENGPVL DDSLPNSVHE YIPFAKDCGNKEKCISDLSLHVAT-
TEKDLLIVRSQNDKFNVSLTVKNTKDSAYNTRTI
VHYSPNLVFSGIEAIQKDSCESNHNITCKVGYP-
FLRRGEMVTFKILFQFNTSYLMENV TIYLSATSD-
SEEPPETLSDNVVNISIPVKYEVGLQFYSSASEYHI-
SIAANETVPEVINSTE
DIGNEINIFYLIRKSGSFPMPELKLSIS-
FPNMTSNGYPVLYPTGLSSSENANCRPHIFEDP FSIN-
SGKKMTTSTDHLKRGTILDCNTCKFATITCNLT-
SSDISQVNVSLILWKPTFIKSYF
SSLNLTIRGELRSENASLVLSSSNQKRELAIQISKDG-
LPGRVPLWVILLSAFAGLLLLML LILALWKIGFFKR-
PLKKKMEK). By way of example, a polypeptide comprising, consisting essentially of, or consisting of the amino acid sequence of SEQ ID NO: 1 sequence can be used to immunize a host in order to produce antibodies that bind specifically to CD49a in accordance with some embodiments. The host organism can be a non-human mammal such as a mouse, rat, guinea pig, rabbit, donkey, goat, or sheep. Isolated antibody-producing cells can be obtained from the host organism, and the cells (or antibody-encoding nucleic acids thereof) can be screened for antibodies that binds specifically to CD49a. In some embodiments, antibody-producing cells are immortalized using hybridoma technology, and the resultant hybridomas are screened for antibodies that bind specifically to CD49a. In some embodiments, antibody-encoding nucleic acids are isolated from antibody-producing cells, and screened for antibodies that bind specifically to CD49a. An example protocol for screening human B cell nucleic acids is described in Huse et al., Science 246:1275-1281 (1989), which is hereby incorporated by reference in its entirety. In some embodiments, nucleic acids of interest are identified using phage display technology (See, e.g., Dower et al., WO 91/17271 and McCafferty et al., WO 92/01047, each of which is hereby incorporated by reference in its entirety). Phage display technology can also be used to mutagenize variable regions (or portions thereof such as CDRs) of antibodies previously shown to have affinity for CD49a. Variant antibodies can then be screened by phage display for antibodies having desired affinity to CD49a. In some embodiments, the antibody that specifically binds to CD49a is formatted as an antigen binding fragment. Example antigen binding fragments suitable for methods, uses, compositions, and pharmaceutical compositions of some embodiments can comprise, consist essentially of, or consist of a construct selected from the group consisting of Fab, Fab', Fab'-SH, $F(ab')_2$, and Fv fragments; minibodies; diabodies; and single-chain fragments such as single-chain Fv (scFv) molecules. Bispecific or multispecific antibodies or antigen binding fragments are also contemplated in accordance with methods, uses, compositions, and pharmaceutical compositions of some embodiments.

In some embodiments, for example if human monoclonal antibodies are of interest, the host comprises genetic modifications to produce or facilitate the production of human immunoglobulins. For example, XenoMouse™ mice were engineered with fragments of the human heavy chain locus and kappa light chain locus, respectively, which contained core variable and constant region sequences (described in detail Green et al. Nature Genetics 7:13-21 (1994), which is hereby incorporated by reference in its entirety). For example, mice have been engineered to produce antibodies comprising a human variable regions and mouse constant regions. The human heavy chain and light chain variable regions can then be reformatted onto a human constant region to provide a fully human antibody (described in detail in U.S. Pat. No. 6,787,637, which is hereby incorporated by reference in its entirety), For example, in a "minilocus" approach, an exogenous Ig locus is mimicked through the inclusion of pieces (individual genes) from the Ig locus. Thus, one or more $V_H$ genes, one or more DH genes, one or more JH genes, a mu constant region, and a second constant region (preferably a gamma constant region) are formed into a construct for insertion into an animal such as a mouse (See, e.g., U.S. Pat. No. 5,545,807, which is hereby incorporated by reference in its entirety). Another approach, includes reconstituting SCID mice with human lymphatic cells, e.g., B and/or T cells. The mice are then immunized with an antigen and can generate an immune response against the antigen (See, e.g., U.S. Pat. No. 5,476,996, which is hereby incorporated by reference in its entirety).

In some embodiments, a host monoclonal antibody is formatted as a chimer antibody or is humanized, so that the antibody comprises at least some human sequences. By way of example, By way of example, an approach for producing humanized antibodies can comprise CDR grafting. For example, an antigen can be delivered to a non-human host (for example a mouse), so that the host produces antibody against the antigen. In some embodiments, monoclonal antibody is generated using hybridoma technology. In some embodiments, V gene utilization in a single antibody producing cell of the host is determined. The CDR's of the host antibody can be grafted onto a human framework. The V genes utilized in the non-human antibody can be compared to a database of human V genes, and the human V genes with the highest homology can be selected, and incorporated into a human variable region framework. See, e.g., Queen, U.S. Pat. No. 5,585,089, which is hereby incorporated by reference in its entirety.

Isolated oligonucleotides encoding a antibody of interest can be expressed in an expression system, such as a cellular expression system or a cell-free system in order to produce an antibody that binds specifically to CD49a in accordance with methods, uses, compositions, and pharmaceutical compositions of embodiments herein. Exemplary cellular expression systems include yeast (e.g., mammalian cells such as CHO cells or BHK cells, *E. coli*, insect cells, *Saccharomyces, Pichia*) transformed with recombinant yeast expression vectors containing the nucleotide sequences encoding antibodies; insect cell systems infected with recombinant virus expression vectors (e.g., baculovirus) containing sequences encoding antibodies; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequences encoding antibodies; mammalian cell systems (e.g., COS, CHO, BHK, 293, 3T3) harboring recombinant expression constructs containing promoters derived from the genome of mammalian cells (e.g., metallothionein promoter) or from mammalian viruses.

In the method or use of some embodiments, the CD49a inhibiting (or blocking) antibody is administered after the onset of the neurological immunity disorder. In the method or use of some embodiments, the administration of the CD49a inhibiting (or blocking) antibody after the onset of the neurological immunity disorder reduces clinical symptoms of the neurological immunity disorder, which can be measured, for example, by a clinical score.

Compositions and Pharmaceutical Compositions

According to some embodiments, a composition or pharmaceutical composition comprises a compound or therapeutic agent and a pharmaceutically acceptable carrier, adjuvant, or vehicle. In some embodiments, the compound or therapeutic agent of the composition or pharmaceutical composition comprises an agent or compound that inhibits (or blocks) integrin signaling. In some embodiments, the compound or therapeutic agent of the composition or pharmaceutical composition comprises an agent or compound that decreases or inhibits CD49a function. In some embodiments, the compound or therapeutic agent of the composition or pharmaceutical composition comprises an antibody or antigen binding fragment which binds CD49a. In some embodiments, the compound or therapeutic agent of the composition or pharmaceutical composition comprises, consists essentially of, or consists of an antibody or antigen binding fragment thereof that binds specifically to CD49a. The antibody or antigen binding fragment thereof that binds specifically to CD49a can be as described herein. In some embodiments the compound or therapeutic agent of the composition or pharmaceutical composition comprises, consists essentially of, or consists of a monoclonal antibody or antigen binding fragment thereof that binds specifically to CD49a. In some embodiments, the composition or pharmaceutical composition is for use in treating, preventing, inhibiting or ameliorateing the relevant disease, disorder, or condition in a subject in need thereof, e.g., neurological immunity disorder or a symptom thereof, such as autism spectrum disorder (ASD), multiple sclerosis (MS), Alzheimer's disease (AD), and/or central nervous system (CNS) injury. It is contemplated that a composition or pharmaceutical composition comprising, consisting essentially of, or consisting of compound that decreases or inhibits CD49a (for example, and anti-CD49a antibody as described herein) can be used in any method of treating, preventing, inhibiting or ameliorateing the relevant disease, disorder, or condition in a subject in need thereof, e.g., neurological immunity disorder or a symptom thereof, such as autism spectrum disorder (ASD), multiple sclerosis (MS), Alzheimer's disease (AD), and/or central nervous system (CNS) injury as described herein.

The amount of therapeutic agent in the composition or pharmaceutical composition of some embodiments is an amount effective to treat, prevent, inhibit or ameliorate the relevant disease, disorder, or condition in a subject in need thereof, e.g., neurological immunity disorder or a symptom thereof, such as autism spectrum disorder (ASD), multiple sclerosis (MS), Alzheimer's disease (AD), and/or central nervous system (CNS) injury. In some embodiments, a composition or pharmaceutical composition is formulated for administration to a subject in need of such composition. In some embodiments, the composition or pharmaceutical composition is formulated for oral administration to a subject. In some embodiments, the composition or pharmaceutical composition is formulated for injection into a subject. In some embodiments, the composition or pharmaceutical composition is formulated for topical application to the skin of the subject. In some embodiments, the subject is an animal, for example a mammal, such as a human.

The term "pharmaceutically acceptable carrier," "adjuvant," or "vehicle" is used herein according to its customary and ordinary meaning as would be understood by one of ordinary skill in the art in view of the specification. It refers to a non-toxic carrier, adjuvant, or vehicle that does not destroy the pharmacological activity of the compound or therapeutic with which it is formulated. Pharmaceutically acceptable carriers, adjuvants or vehicles that may be used in the compositions and pharmaceutical compositions of some embodiments herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the composition or pharmaceutical composition comprising an anti-CD49a antibody comprises a buffer, such as an acetate, histidine, succinate, or phosphate buffer. The buffer can be at a concentration of about 10 mM to about 50 mM, for example, about 20 mM to about 40 mM, such as about 30 mM. For example, the composition can contain a histidine buffer at a concentration of about 10 mM to about 50 mM, for example, about 20 mM to about 40 mM, such as about 30 mM. In one embodiment, the composition contains an acetate buffer at a concentration of about 10 mM to about 50 mM, for example, about 20 mM to about 40 mM, such as about 30 mM.

In some embodiments, the composition or pharmaceutical composition comprises an excipient, such as sorbitol, sodium chloride (NaCl), sucrose, trehelose, or mannitol. The composition can include an excipient at a concentration of about 100 mM to about 300 mM, for example, 110 mM to about 270 mM, about 120 mM to about 230 mM, or about 130 mM to about 210 mM, about 170 mM to about 200 mM, or about 180 mM to about 200 mM. For example, the composition can contain sorbitol at a concentration of about 180 mM to about 300 mM, for example, about 200 mM to about 300 mM, about 200 mM to about 240 mM, about 230 mM to about 270 mM, or about 240 mM to about 260 mM. In another example, the composition can contain NaCl at a concentration of about 100 mM to about 200 mM, for example, about 110 mM to about 190 mM, about 120 mM to about 180 mM, or about 130 mM to about 170 mM. In another example, the composition can contain sucrose at a concentration of about 200 mM to about 240 mM, about 230 mM to about 270 mM, or about 240 mM to about 260 mM. In another example, the composition can contain trehalose at a concentration of about 200 mM to about 240 mM, about 230 mM to about 270 mM, or about 240 mM to about 260 mM. In yet another example, the composition can contain mannitol at a concentration of about 200 mM to about 240 mM, about 230 mM to about 270 mM, or about 240 mM to about 260 mM.

In some embodiments, the aqueous composition or pharmaceutical composition comprises a surfactant, e.g., a substance that lowers surface tension of a liquid, such as a polysorbate, for example, polysorbate 80 or polysorbate 20. In some embodiments, the concentration of surfactant is at a concentration of about 0.001% to about 0.5%, about 0.001% to about 0.1%, for example, about 0.005% to about 0.05%, such as about 0.01%. Compositions or pharmaceutical compositions of some embodiments herein may be administered orally, parenterally, by inhalation spray, topically, rectally, nasally, buccally, vaginally or via an implanted reservoir. The term "parenteral" is used herein according to its customary and ordinary meaning as would be understood by one of ordinary skill in the art in view of the specification. It includes subcutaneous, intravenous, intramuscular, intra-articular, intra-synovial, intrasternal, intrathecal, intrahepatic, intralesional and intracranial injection or infusion techniques. The compositions may be administered orally, intraperitoneally or intravenously. Sterile injectable forms of the compositions or pharmaceutical compositions of some embodiments herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

In some embodiments, the composition or pharmaceutical composition is administered by an oral, intravenous, subcutaneous, intranasal, inhalation, intramuscular, intraocular, intraperitoneal, intratracheal, transdermal, buccal, sublingual, rectal, topical, local injection, or surgical implantation route. In some embodiments, the administration route is oral. In some embodiments, the administration is via injection. In some embodiments, the administration is via local injection. In some embodiments, the administration of the compound is into the cerebrospinal fluid (CSF) of said subject. In some embodiments, the administration of the compound is via intracerebroventricular injection. In some embodiments, the administration is transdermal, e.g., via application of an ointment containing the therapeutic to the head (scalp skin) of said subject.

To aid in delivery of the composition or pharmaceutical composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Compositions or pharmaceutical compositions of some embodiments may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, compositions or pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions or pharmaceutical compositions of some embodiments may also be administered topically, especially when the target of treatment includes areas or organs readily accessible by topical application, such as the skin (e.g., scalp skin), or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided compositions or pharmaceutical compositions of some embodiments may be formulated in a suitable ointment containing the active component suspended or dissolved in one or more carriers. Carriers for topical administration of a therapeutic include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Provided compositions or pharmaceutical compositions of some embodiments may be formulated as micronized suspensions in isotonic, pH adjusted sterile saline, or, preferably, as solutions in isotonic, pH adjusted sterile saline, either with or without a preservative such as benzylalkonium chloride. Alternatively, the pharmaceutically acceptable compositions may be formulated in an ointment such as petrolatum.

Compositions or pharmaceutical compositions of some embodiments may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, compositions or pharmaceutical compositions are formulated for oral administration. Such formulations may be administered with or without food. In some embodiments, pharmaceutically acceptable compositions are administered without food. In some embodiments, compositions or pharmaceutical compositions of are administered with food.

The amount of therapeutic that may be combined with the carrier materials to produce a composition or pharmaceutical composition in a single dosage form will vary depending upon the host treated, the particular mode of administration, and other factors known to one of ordinary skill. Preferably, provided compositions should be formulated so that a dosage of between 0.01-100 mg/kg body weight/day of the therapeutic agent can be administered to a patient receiving these compositions.

It should also be understood that a specific dosage and treatment regimen for any particular patient will depend upon a variety of factors, including the activity of the specific therapeutic employed, the age, body weight, general health, sex, diet, time of administration, rate of excretion, drug combination, and the judgment of the treating physician and the severity of the particular disease being treated. The amount of a therapeutic in the composition will also depend upon the particular therapeutic in the composition.

Compositions or pharmaceutical compositions of some embodiment comprising a therapeutic and a pharmaceutically acceptable excipient, diluent, or carrier, are useful for treating a variety of diseases, disorders or conditions. Such diseases, disorders, or conditions include those described herein. In the method or use of some embodiments, the therapeutically effective amount of the compound is about 0.0002 mg/kg to about 2.0 mg/kg. In further embodiments, said therapeutically effective amount of the compound is about 0.00020 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, or about 2.0 mg/kg.

In the method or use of some embodiments, said therapeutically effective amount of the compound is less than about 0.00020 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, or about 2.0 mg/kg.

In the method or use of some embodiments, said therapeutically effective amount of the compound is more than about 0.00020 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, or about 2.0 mg/kg.

Methods, uses, and compositions of some embodiments include an aqueous pharmaceutical composition, such as a stable aqueous pharmaceutical composition, containing an anti-CD49a antibody at a concentration of about 100 mg/mL to about 225 mg/mL, for example, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 205 mg/mL, about 210 mg/mL, about 215 mg/mL, about 220 mg/mL or about 225 mg/mL.

In the method or use of some embodiments, the compound is administered into the cerebrospinal fluid (CSF) of the subject. In the method or use of some embodiments, an ointment comprises said compound and the ointment is administered via application of the ointment to the scalp skin of the subject. In the method or use of some embodiments, an ointment comprises said compound and the ointment is administered via application of the ointment to the head of the subject.

In the method or use of some embodiments, the administration of said compound results in accumulation of immune cells in the brain meninges. In the method or use of some embodiments, the administration of said compound results in elevated T cells and/or natural killer T (NKT) cells in the brain parenchyma.

A compound referred to herein as one that "blocks" integrin signaling may also be referred to herein as a compound that "inhibits" integrin signaling. It will be understood that use of the term "inhibit" or "block" is not intended to necessitate absolute inhibition (or blockage), and as such inhibition or (blockage) as used herein also includes a decrease, reduction or impairment of the relevant target or function. For example, an antibody or antigen binding fragment thereof that binds specifically to CD49a may be referred to herein as a "CD49a-specific" antibody, "anti-CD49a" antibody, CD49a "inhibiting" antibody, and/or CD49a "blocking" antibody. In the method or use of some embodiments, the compound that inhibits integrin signaling comprises, consists essentially of, or consists of Tysabri (natalizumab) or an antigen binding fragment thereof. In the method or use of some embodiments, the compound that inhibits integrin signaling is a compound other than Tysabri (natalizumab). In the method or use some embodiments, the compound that inhibits integrin signaling comprises, consists of, or consists essentially of Tysabri® (natalizumab) formulated for administration into the CSF of the subject or as an ointment to the head of the subject. In the method or use of some embodiments, the compound that inhibits integrin signaling comprises, consists essentially of, or consists of ReoPro® (Abcizimab), Vedolizumab, etrolizumab, anti-av integrin, or Volocixmab, or a combination of two or more of these. In the method or use of some embodiments, the compound that inhibits integrin signaling is ReoPro® (Abcizimab), Vedolizumab, etrolizumab, anti-av integrin, or Volocixmab. In the method or use of some embodiments, the compound that inhibits integrin signaling is a compound other than ReoPro® (Abcizimab), Vedolizumab, etrolizumab, anti-av integrin, or Volocixmab.

In methods, uses, compositions, and pharmaceutical compositions of some embodiments, the anti-CD49a antibody as described herein binds to and inhibits the activity of CD49a by at least 50% (e.g., 60%, 70%, 80%, 90%, 95% or greater, including any increment therein). The apparent inhibition constant ($Ki^{app}$ or $K_{i,app}$), which provides a measure of inhibitor potency, is related to the concentration of inhibitor required to reduce target (e.g., CD49a) activity and is not dependent on target concentrations. The inhibitory activity of an anti-CD49a antibody described herein can be determined by methods known in the art. In some embodiments, the anti-CD49a binds to CD49a with a dissociation constant $K_D$ that is numerically lower (indicating tighter binding than) $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$, including ranges between any two of the listed values. A $K_D$ can be determined using methods known in the art, for example surface plasmon resonance on a BIACORE apparatus.

The $K_{i,}^{app}$ value of an antibody may be determined by measuring the inhibitory effect of different concentrations of the antibody on the extent of the reaction (e.g., target activity such as CD49a activity); fitting the change in pseudo-first order rate constant (v) as a function of inhibitor concentration to the modified Morrison equation (Equation 1) yields an estimate of the apparent Ki value. For a competitive inhibitor, the $Ki^{app}$ can be obtained from the y-intercept extracted from a linear regression analysis of a plot of $K_{i,}^{app}$ versus substrate concentration.

$$v = A \cdot \frac{([E]-[I]-K_i^{app}) + \sqrt{([E]-[I]-K_i^{app})^2 + 4[E] \cdot K_i^{app}}}{2} \quad \text{(Equation 1)}$$

Where A is equivalent to $v_o/E$, the initial velocity ($v_o$) of the enzymatic reaction in the absence of inhibitor (I) divided by the total enzyme concentration (E).

In some embodiments, the anti-CD49a antibody described herein has a Kiapp value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for the target antigen or antigen epitope, such as an epitope of CD49a. Differences in Kiapp (e.g., for specificity or other comparisons) can be at least 1.5, 2, 3, 4, 5, 10, 15, 20, 37.5, 50, 70, 80, 91, 100, 500, 1000, 10,000 or 105 fold. In some examples, the anti-CD49a antibody inhibits a first antigen (e.g., a first protein in a first conformation or mimic thereof) better relative to a second antigen (e.g., the same first protein in a second conformation or mimic thereof; or a second protein). In some embodiments, any of the anti-CD49a antibodies may be further affinity matured to reduce the Kiapp of the antibody to the target antigen or antigenic epitope thereof.

In methods, uses, compositions, and pharmaceutical compositions of some embodiments, the anti-CD49a antibody suppresses or inhibits integrin signaling triggered by CD49a by at least 50% (e.g., 60%, 70%, 80%, 90%, 95% or greater, including any increment therein). Such inhibitory activity can be determined by conventional methods.

EXAMPLES

In the following Examples, CD49a is identified as a marker that can differentiate two distinct populations of meningeal T cells and that blockade of CD49a, using a blocking antibody in vivo, results in the accumulation of numerous populations of immune cells in the meninges and the parenchymal infiltration of NKT and T cells.

Figure 1F:
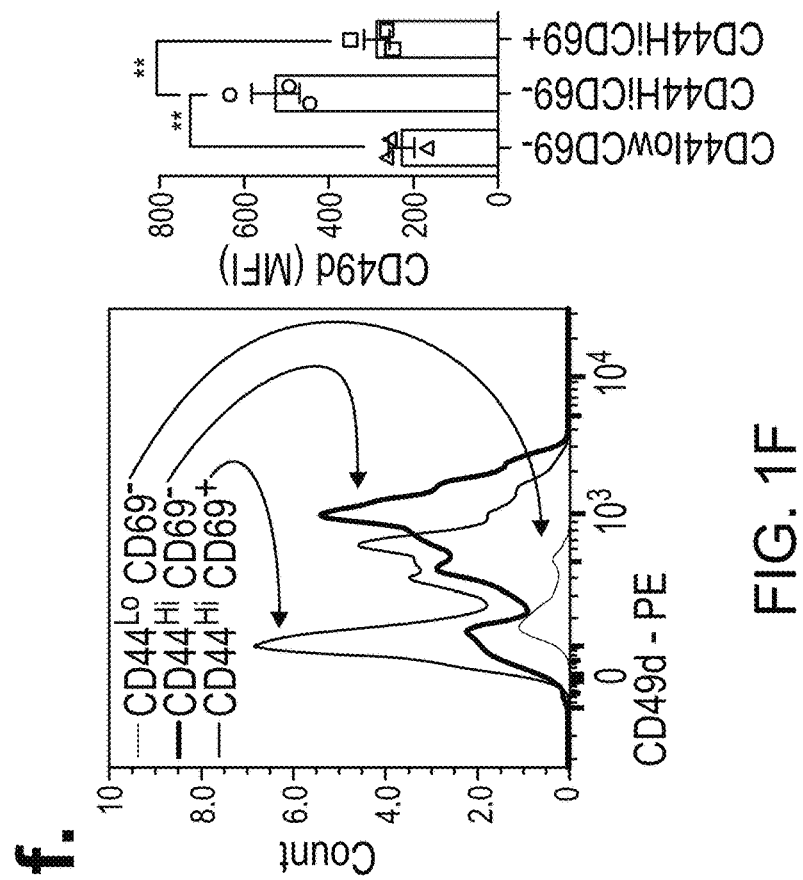
Figure 1E:
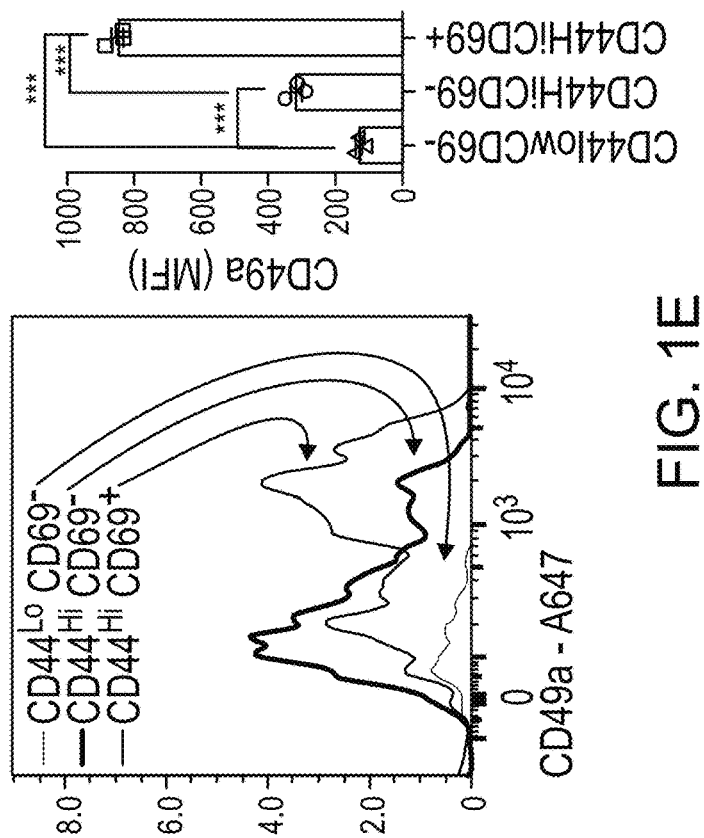

Example 1: Naïve Meninges are Composed of Distinct Populations of CD4 T Cells Meningeal CD4 T cells have been shown to support cognitive function, in part through the secretion of cytokine IL-4[8]. In order to further analyze the different populations of T cells that populate the naïve meninges, both meninges and diaphragm were isolated and analyzed from adult mice. As described before[8], the majority of T cells in the meninges express CD44 and half of the CD44+ cells also express the activation marker CD69 (FIGS. 1a,b). In recent years, a new population of tissue resident memory T cells (or TRM) was described in mucosal tissues after infection, where they ensure surveillance of the tissue against secondary infection[11-14]. One of the markers that characterize the TRM is the high expression of CD69[14]. Therefore the CD69– and CD69+ populations of meningeal CD4 T cells were analyzed for the expression of other TRM markers. Indeed the CD69+ population of CD4 T cells of the meninges expresses high levels of CD11a and CD49a, but no CD103 (FIGS. 1c-e), consistent with TRM CD4 T cells identified in the periphery[11-14]. CD49d, an integrin implicated in the recirculation of T cells in the CNS[8] is mostly express by the CD69– CD4 T cells suggesting that the CD69+ T cells are less likely to be recirculating, a common feature of TRM T cells (FIG. 1f).

Example 2: CD49a is Expressed by Multiple Immune Populations in the Meninges and Its Blockade Results in the Transient Accumulation of Immune Cells in the Meninges CD49a is an integrin alpha subunit, expressed by multiple cell types throughout the body[15], notably by immune cells[15], and is especially implicated in homing of immune cells in specific tissues. The expression of CD49a by the immune cells that populate the naïve meninges was analyzed. Not only CD4 T cells express CD49a, but also CD8 and NK cells, and to a greater extent NKT cells and monocytes/macrophages (FIGS. 2a,b).

To test the role of CD49a on meningeal immune cells, CD49a interaction and signaling was blocked by using a blocking antibody[16]. Surprisingly, intracerebroventricular (i.c.v.) injection of a CD49a-blocking antibody [purchased from BD Biosciences, Catalog No. 553961, Clone Ha4/8] at about 5 µg in 5 µL volume resulted in increased numbers of immune cells previously shown to express high level of CD49a, i.e. T cells, NK cells, and monocytes/macrophages, as soon as 24h after the antibody injection (FIG. 2c,d). CD49a being an integrin allowing the interaction of immune cells with their local ECM, blockade of CD49a might solely facilitate the extraction of the meningeal immune cells during the tissue isolation. To confirm this, immunohistochemistry was used on meningeal whole mount, 24 h after icy injection of the anti-CD49a antibody. Similar to the FACS analysis, there was an increased density of CD45+ and CD3+ T cells around the sinuses of anti-CD49a-injected mice (FIGS. 2e-g). The accumulation of immune cells in such a small window of time can be due to local proliferation or active recruitment of cells in the meninges. To try and answer this question, pulsed mice were pulsed with BrdU to assess the proliferative state of the cells after CD49a treatment. There was an increase of BrdU+ CD4 T cells in the meninges 24h after icy injection of CD49a blocking antibody (FIGS. 2h,i), suggesting, at least in part, that CD49a induces proliferation of meningeal immune cells. The duration of CD49a blocking effect was then tested. Mice were injected i.c.v. with the anti-CD49a antibody and sacrificed at different time points post injection. Analysis of the meningeal T cells number revealed an increased number of meningeal T cells up to 3 days after CD49a blockade (FIG. 2j). Interestingly no change in immune cell numbers was observed in the draining (deep cervical) or control (inguinal) lymph nodes, suggesting a local effect of the CD49a blockade antibody.

Figures 3A, 3B:
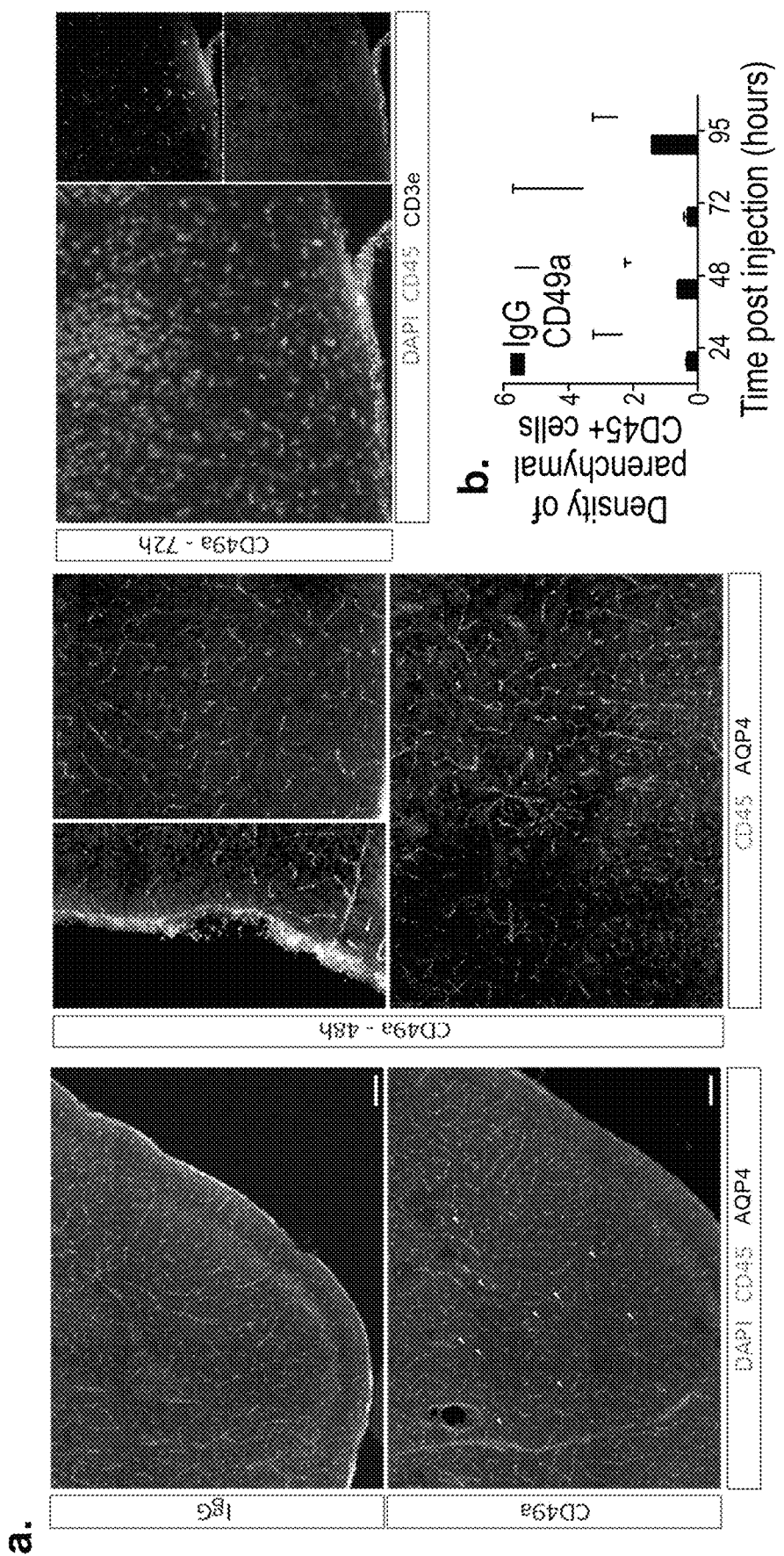
FIGS. 3A-3E show that blockade of CD49a induces the parenchymal infiltration of immune cells.
Figures 3C, 3D:
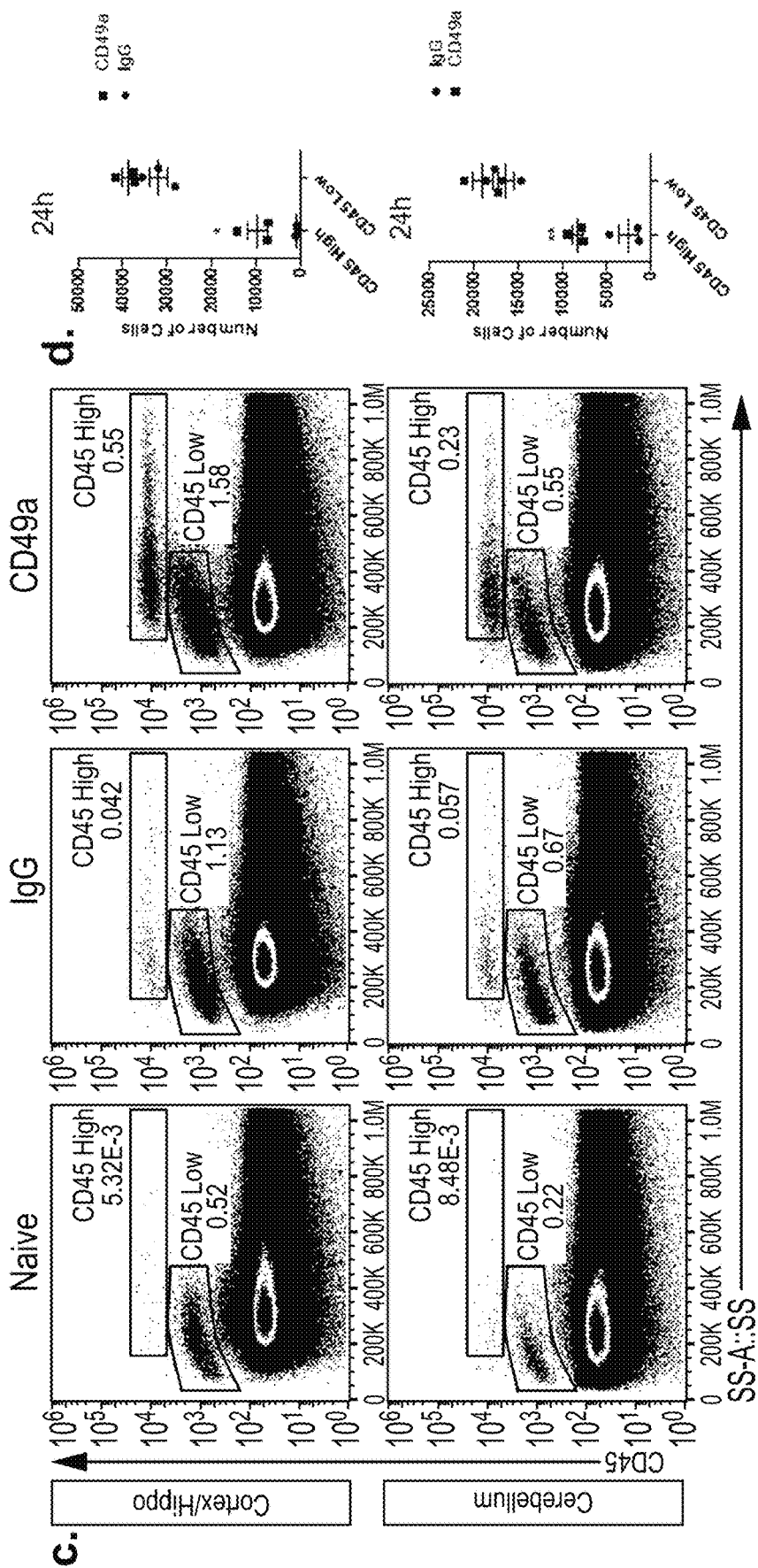
Figure 3E:
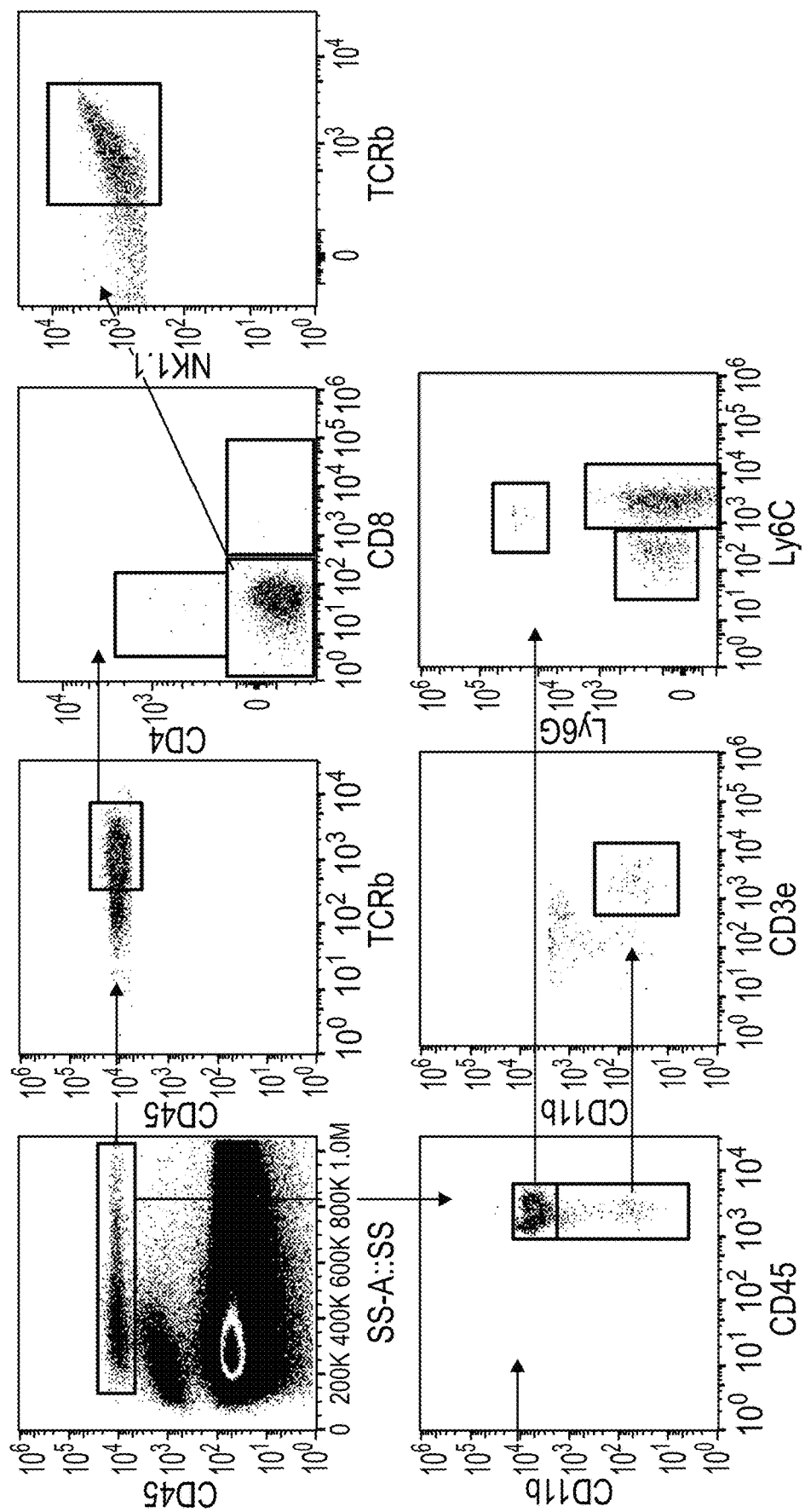
Figure 4C:
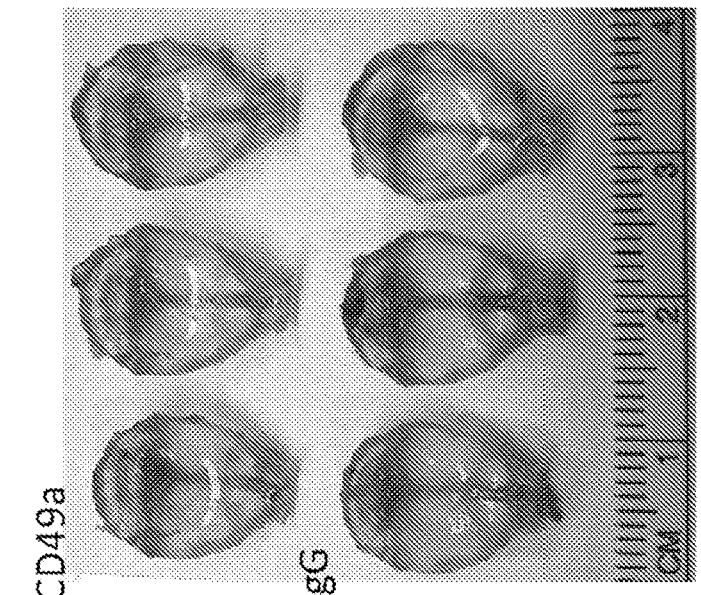
Figure 4B:
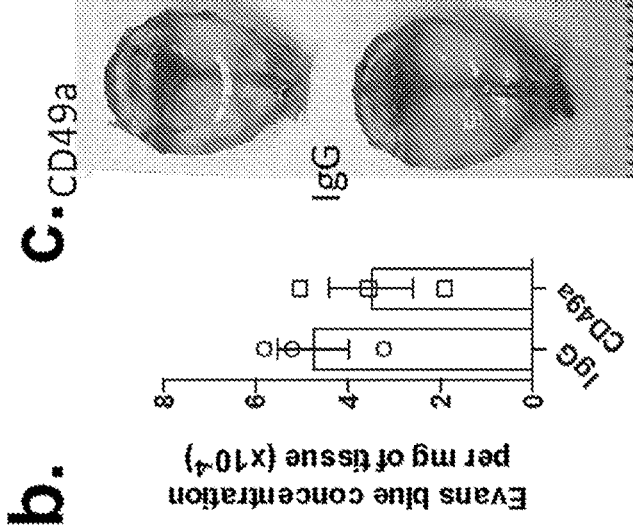

Example 3: CD49a Blockade Results in the Parenchymal Infiltration of T Cells and NKT Cells, Most Likely Through a Trans-Pial Migration I.c.v. injection of the CD49a blockade antibody results in elevated numbers of immune cells in the meningeal compartment. The next example was to show CD49a blockade also resulted in infiltration of immune cells into the brain parenchyma. Brains from CD49a injected mice were then analyzed by both flow cytometry and IHC for the presence of intraparenchymal immune cells. Labeling of brain slices with anti-CD45 antibody revealed the presence of roundly shaped immune cells within the brain parenchyma of CD49a-injected mice as soon as 24 h after the injection (FIG. 3a). Those cells are not trapped into blood or perivascular spaces, as seen with the AQP4 staining and sometimes form clusters within the parenchyma (FIG. 3a). Similar infiltration can be found for up to 4 days after the anti-CD49a injection (FIG. 4b). FACS analysis of the cortex, cerebellum, and spinal cord of CD49a antibody injected mice revealed a spatial specificity of the infiltrate with no detectable immune infiltrate in the spinal cord of CD49a injected mice but a large infiltrate in both the cortex and cerebellum of injected mice (FIGS. 3c-d). The phenotype of the infiltrated immune cells was assessed and found that the majority of them are TCRb+CD4-CD8-NK1.1+, but also CD11b+Ly6C+, suggesting a population of activated NKT cells. Small populations of CD4+ and CD8+ T cells are also found (FIG. 3e).

Figure 4A:

Not only is CD49a expressed by immune cells but also by the blood endothelial cells[15]. To confirm that the parenchymal infiltration of immune cells upon CD49a blockade is not related to a transient opening of the blood brain barrier (BBB), the integrity of the BBB was tested by injecting Evans Blue in the blood vasculature during the 24 h after CD49a treatment. As seen in FIGS. 4a-c, no Evans Blue was detected in the brain or the meninges of IgG or CD49a treated mice, suggesting that the BBB remained intact during the treatment and that the parenchymal infiltration of immune cells is unlikely to come from an opening of the BBB or the BMB (blood meningeal barrier) Immune cells could however infiltrate the parenchyma directly from the meninges, either by crossing the pia or by infiltrating the Virchow-Robin spaces. To confirm this, the KiKGR mice that bear a photoconvertable protein and enables tracking the cell were used. Meninges of KiKGR mice were photoconverted (Green to Red) with a UV laser following i.c.v. injection of CD49a (FIG. 3d). Twenty-four hours after the injection, brains were harvested and the fluorescence of the infiltrated T cells was analyzed by FACS. Indeed, around 25% of the CD45 high cells found in the brain of CD49a injected mice are photoconverted (red) suggesting that those cells were localized in the meninges during the photoconversion (FIG. 3e). These results strongly suggest that the infiltrated immune cells trafficked from the meninges directly into the brain parenchyma.

Overall, blocking the integrin signaling through CD49a induces the proliferation and migration of specific immune cells from the meninges to the brain parenchyma.

Example 4: Repetitive Blockade of CD49a Results in a Decrease in EAE Scoring

Figure 5:
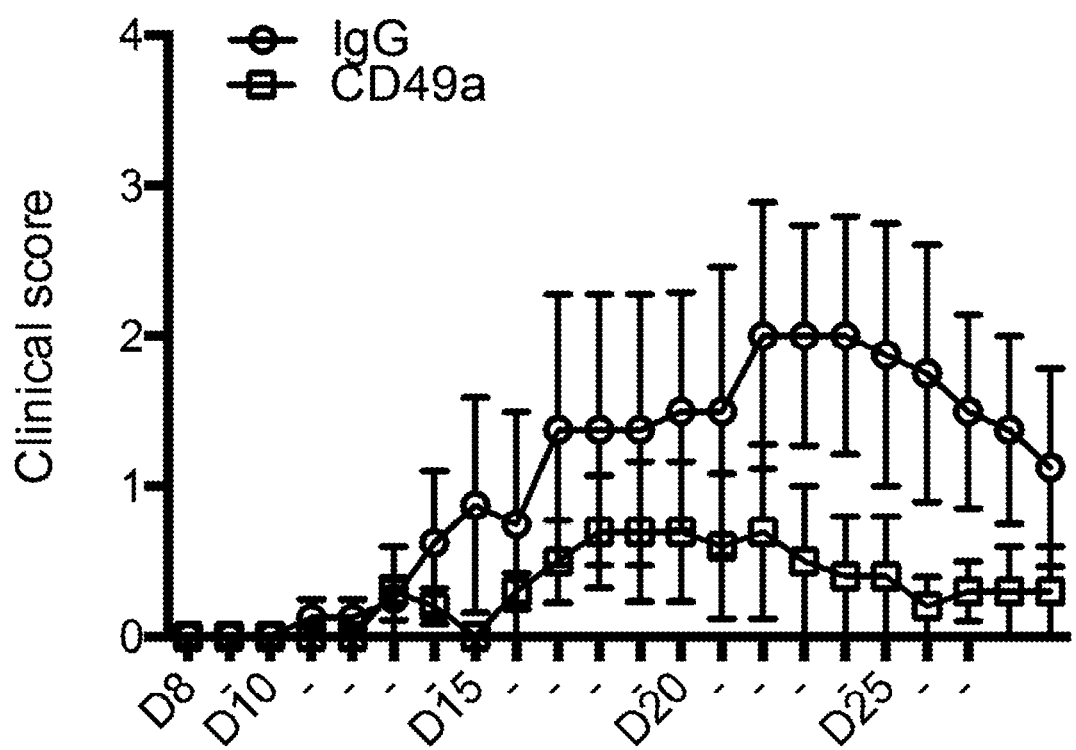
FIG. 5 shows the effect of repeated anti-CD49a injection on the development of EAE. Mice were injected i.c.v. with anti-CD49a or IgG antibodies every other day from six days before the induction of EAE to fifteen days after induction. Clinical score of mice treated with IgG and anti-CD49a antibodies. Preliminary data suggest that CD49a treatment limited the development of clinical symptoms of EAE.

Blockade of CD49a interaction and signaling results in the accumulation of T cells and NKT cells in the brain parenchyma of WT mice, likely coming from endogenous meningeal immune cells. The next example shows blocking of CD49a interferes with the development of EAE, the animal model of Multiple Sclerosis, where immune cells, notably T cells, transit through the meninges and also infiltrate the parenchyma. Catheters were inserted into the cisterna magna into mice and were injected every other day with about 5 µg in 5 mL of the CD49a blockade antibodies. At day 6 after beginning of CD49a treatment, EAE was induced by injection of an emulsion of MOG35-55 subcutaneously above the tail. Surprisingly, the repetitive injection of CD49a blocking antibodies decreased the diseases severity compared to IgG injected mice, showing a protective effect of CD49a blockade in the development of EAE (FIG. 5).

Overall those data show that interfering with an integrin, highly expressed by the meningeal immune cells, is sufficient to induce drastic changes in local immune cell populations and favor the migration of cells into the brain parenchyma. CD49a is an example of one integrin that controls immune cell localization and function within brain borders.

Figure 6A:
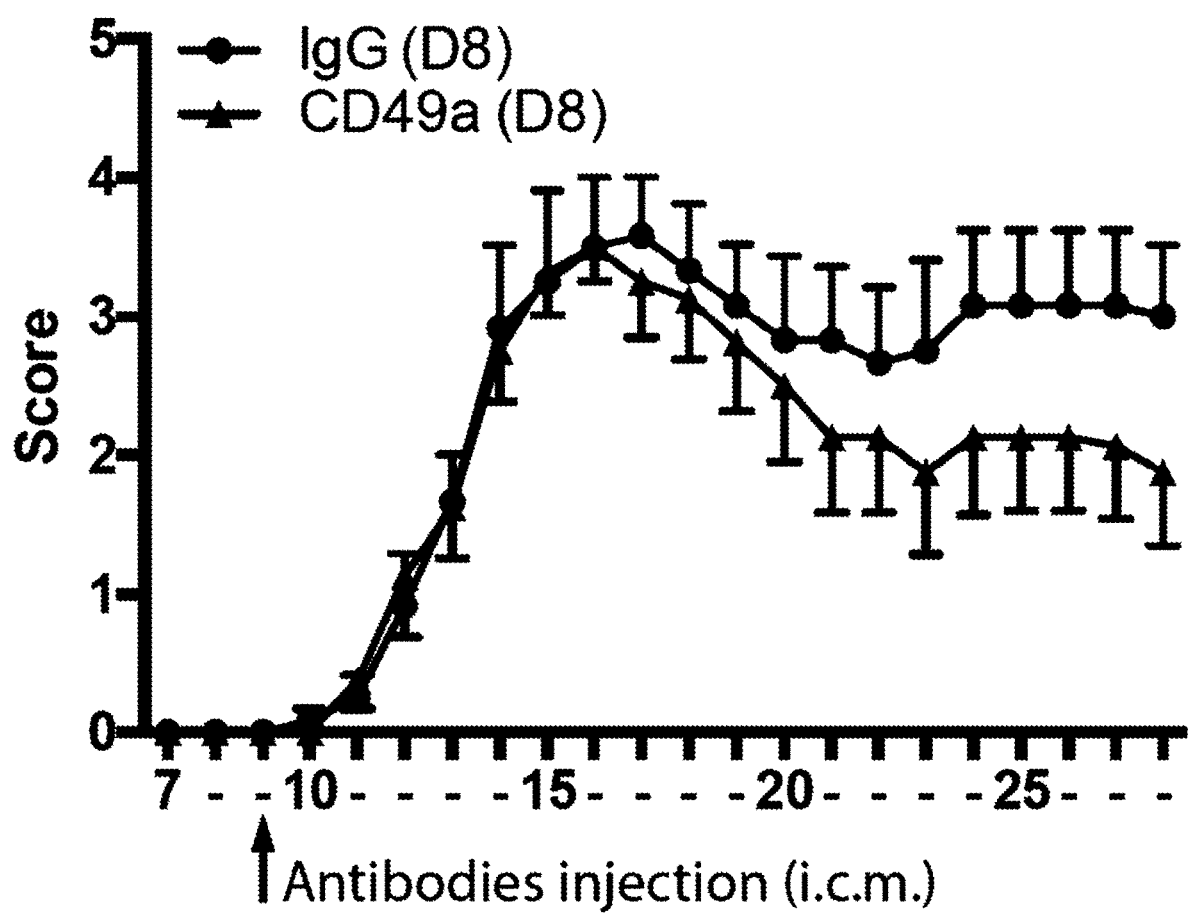
FIGS. 6A-B are each graphs illustrating effects of i.c.m. administration of anti-CD49a antibody on disease progression of EAE. Adult C57Bl6 female mice were injected i.c.m. with 5 µl of anti-CD49a antibody (or IgG control) at day 8 post EAE induction (EAE was induced by 200 µg of MOG$_{35-55}$+CFA). Mice were subsequently followed daily for disease progression. CD49a-treated mice appeared to have ameliorated progression of symptoms compared to IgG-treated mice.
Figure 6B:
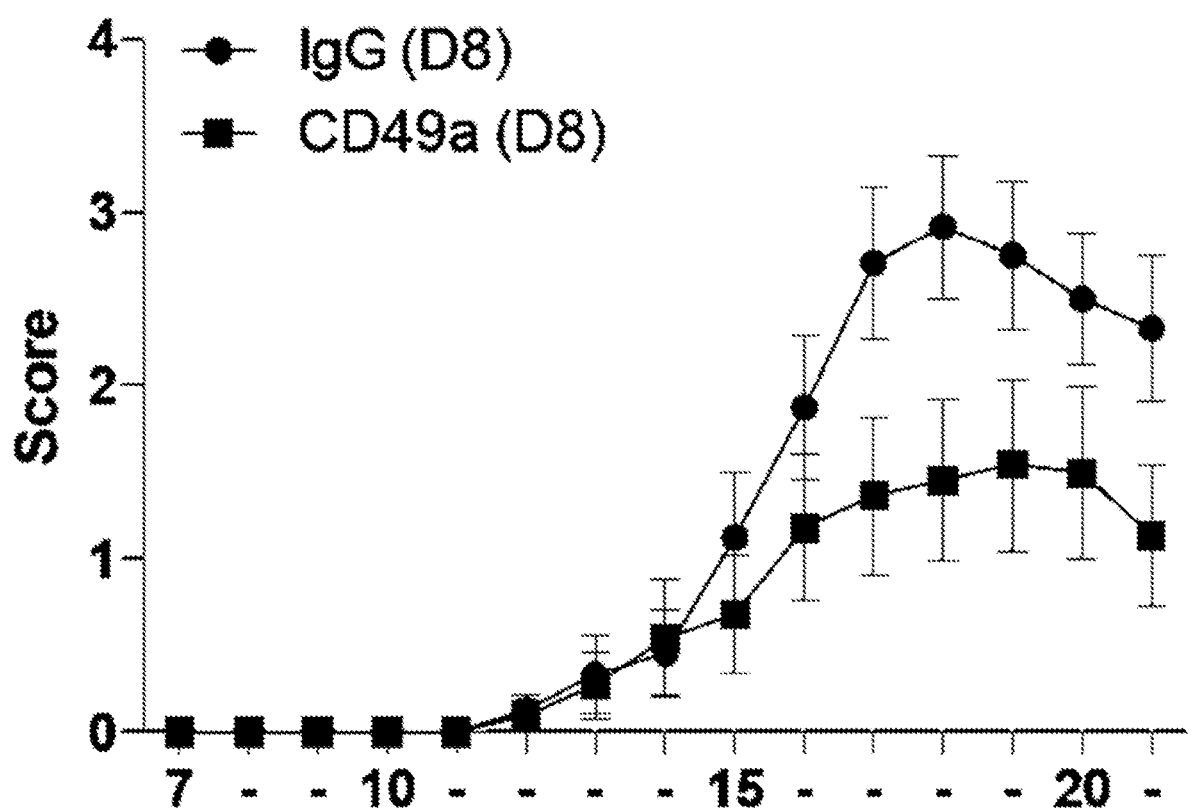

Example 5: Administration of an Antibody that Inhibits CD49a Results in a Decrease in EAE Score Adult C57Bl6 female mice were injected i.c.m. with 5 µl of anti-CD49a antibody (or IgG control) at day 8 post EAE induction (EAE was induced by 200 µg of MOG$_{35-55}$+CFA). Mice were subsequently followed daily for disease progression. The results of this experiment are shown in FIG. 6A. An additional repetition of this experiment is shown in FIG. 6B. CD49a-treated mice show ameliorated progression of symptoms compared to IgG-treated mice.

Example 6: Modulation of a CD49a Blockade

Figure 7A:
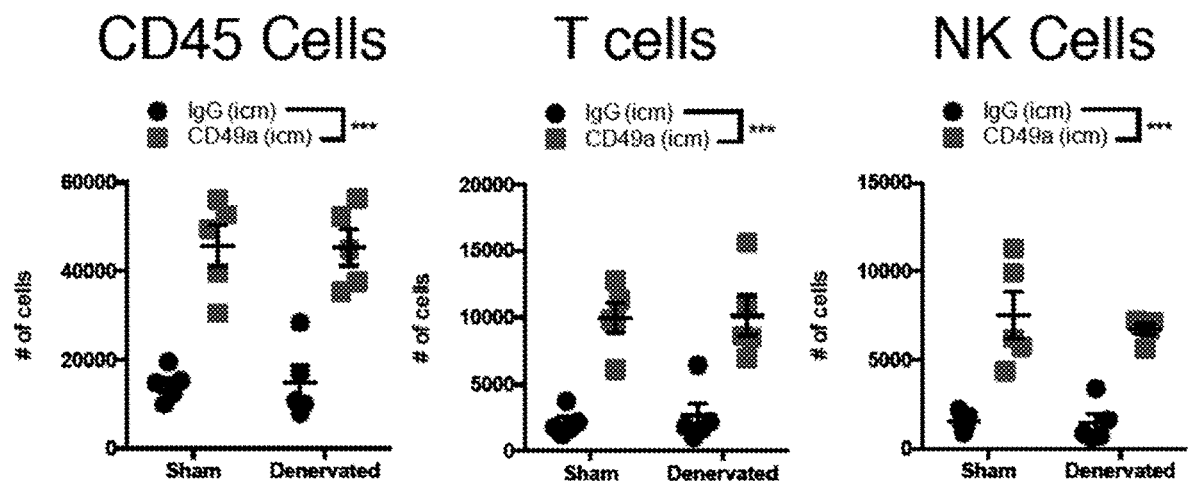
FIGS. 7A-B are each graphs showing quantification of immune cells in surgically denervated mice.
Figure 7B:
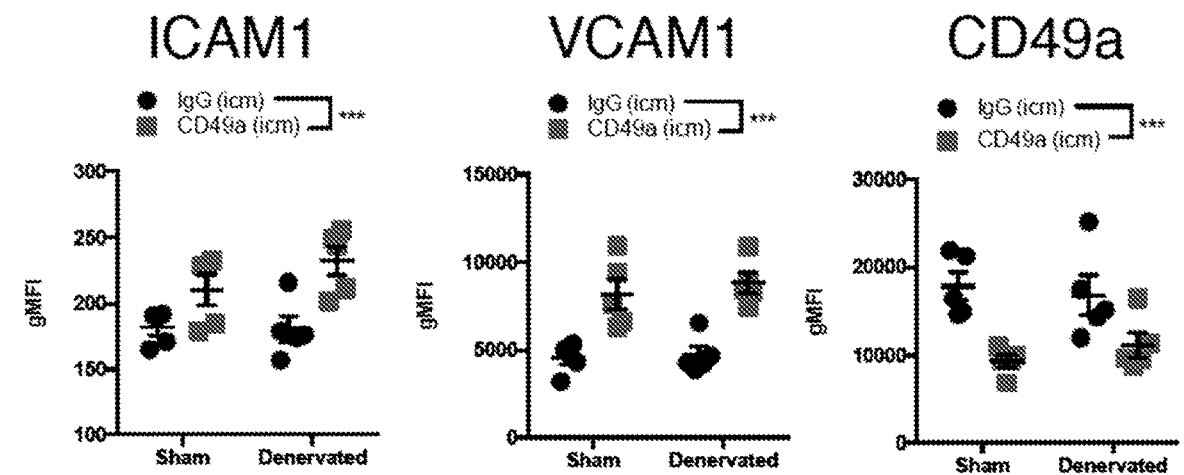

Adult C57B16 mice where sham operated or denervated (SCG excision). One week after surgery, mice were injected with 5 µg of anti-CD49a (or IgG) and tissues were harvested 24h after. FIG. 7A shows quantification of the number of CD45+, T cells, and NK cells in the meninges of sham or denervated IgG and CD49a treated mice. (mean±s.e.m.; n=5 mice/group, *p<0.001, two-way ANOVA). FIG. 7B shows quantification of geometric mean fluorescence intensity for ICAM1, VCAM1 and CD49a by the meningeal endothelial cells of sham or denervated IgG and CD49a treated mice. (mean±s.e.m.; n=5 mice/group, *p<0.001, two-way ANOVA). Thus, administering an inhibitor of CD49a signaling to an EAE subject (a model of MS) in accordance with some embodiments herein increased immune cells in the meninges, regardless of whether the subject was denervated (by excision of the SCG).

Figure 8A:
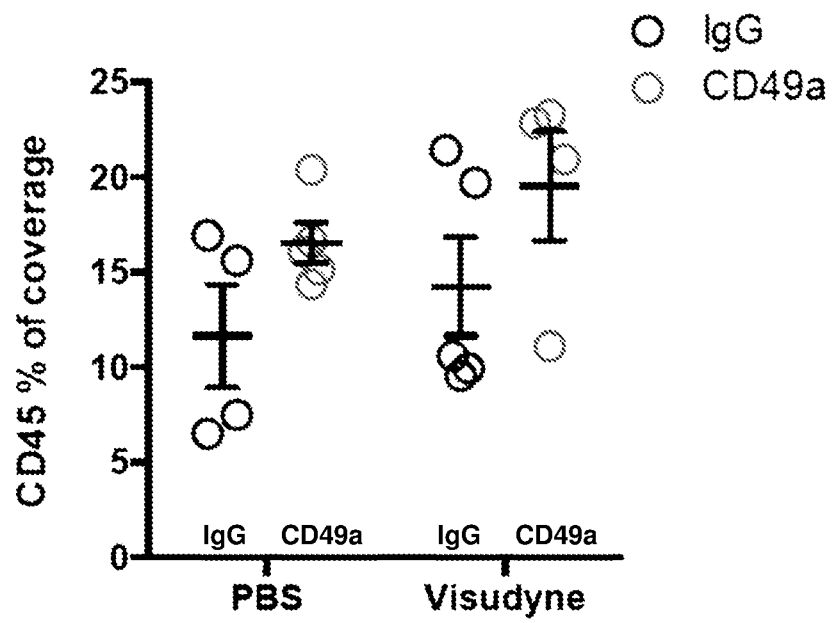
FIGS. 8A-D are each graphs showing quantification of immune cells in the SSS of mice that underwent meningeal lymphatic ablation with visodyne.
Figure 8B:
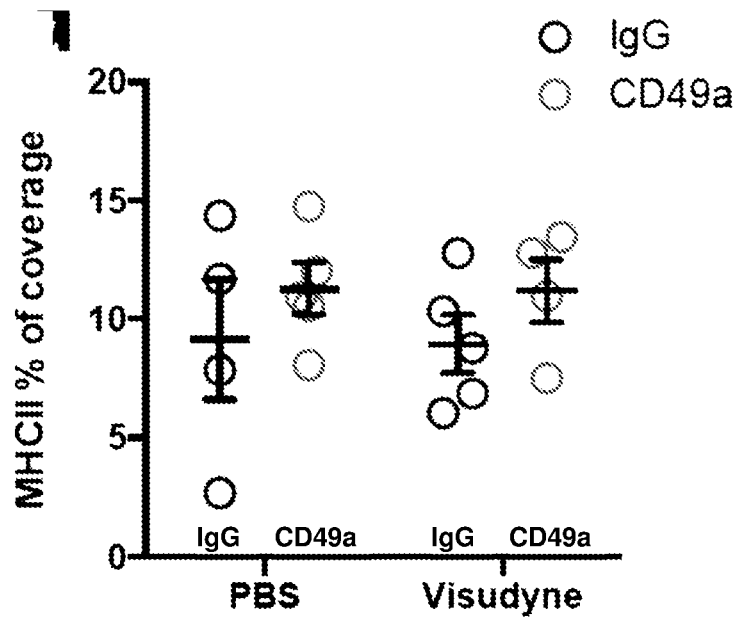
Figure 8C:
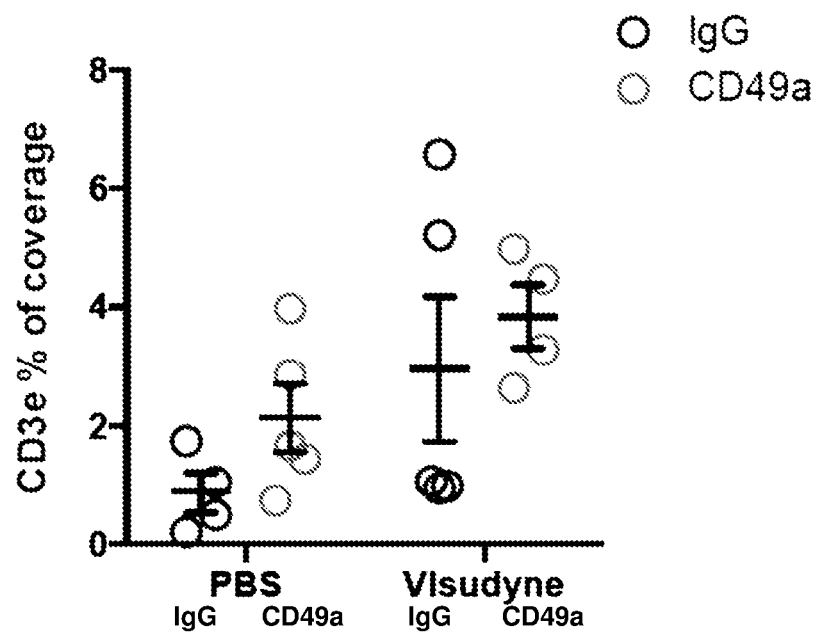
Figure 8D:
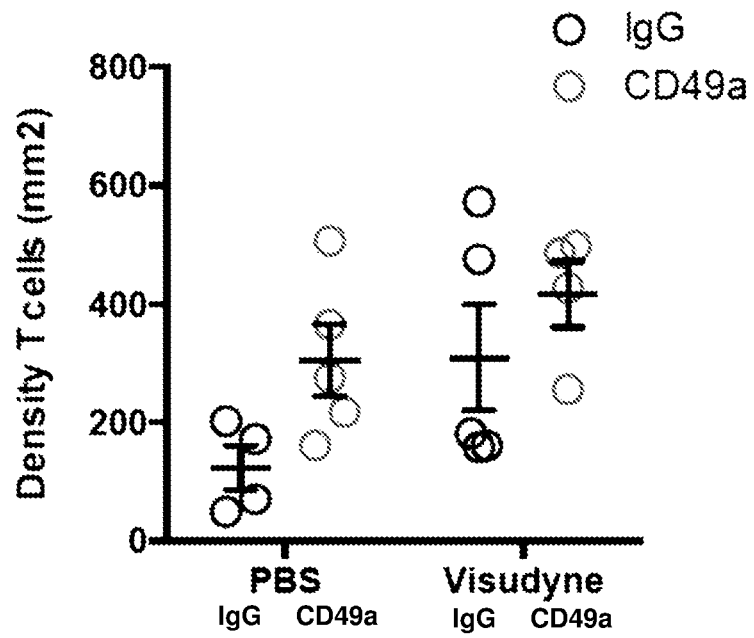

Adult C57B16 mice had their meningeal lymphatic vessels ablated using Visudyne (control mice were injected with PBS). One week after meningeal lymphatic ablation, mice were injected with 5 µg of anti-CD49a (or IgG) and tissues were harvested 24 h after injection. FIG. 8A shows quantification of the CD45 coverage in the SSS of mice. (mean±s.e.m.; n=4/5 mice/group). FIG. 8B shows quantification of the MHCII coverage in the SSS of mice. (mean±s.e.m.; n=4/5 mice/group). FIG. 8C shows Quantification of the CD3e coverage in the SSS of mice. (mean±s.e.m.; n=4/5 mice/group). FIG. 8D shows Quantification of the density of CD3e cells in the SSS of mice. (mean±s.e.m.; n=4/5 mice/group). Thus, administering an inhibitor of CD49a signaling to an EAE subject (a model of MS) in accordance with some embodiments herein increased immune cells in the SSS, regardless of whether the subject had undergone meningeal lymphatic ablation.

Figure 9A:
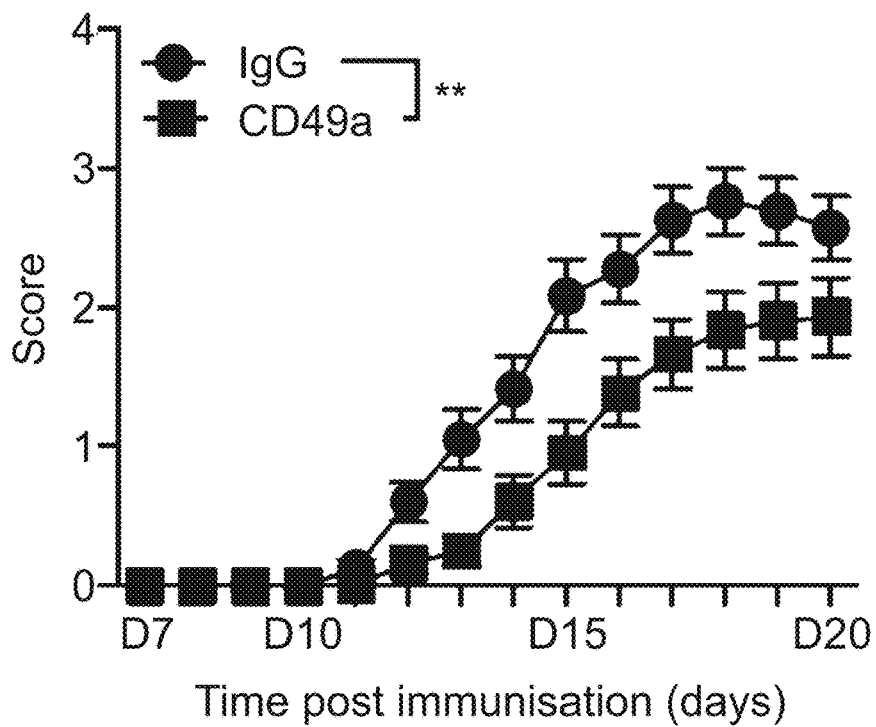
FIGS. 9A-C are each graphs showing clinical effects of anti-CD49a treatment in accordance with some embodiments herein.
Figure 9B:
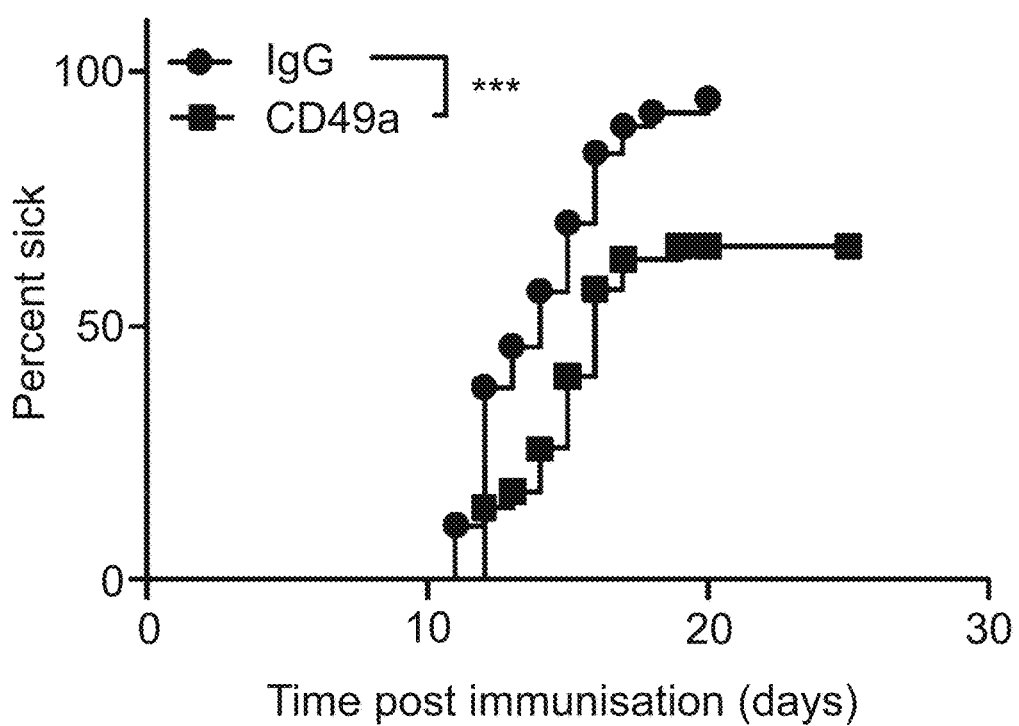
Figure 9C:
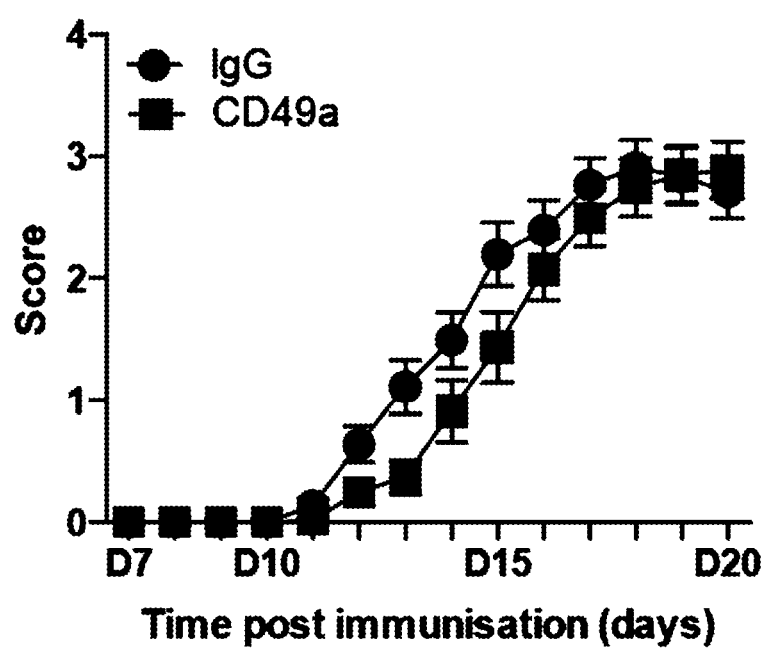
Figure 9D:
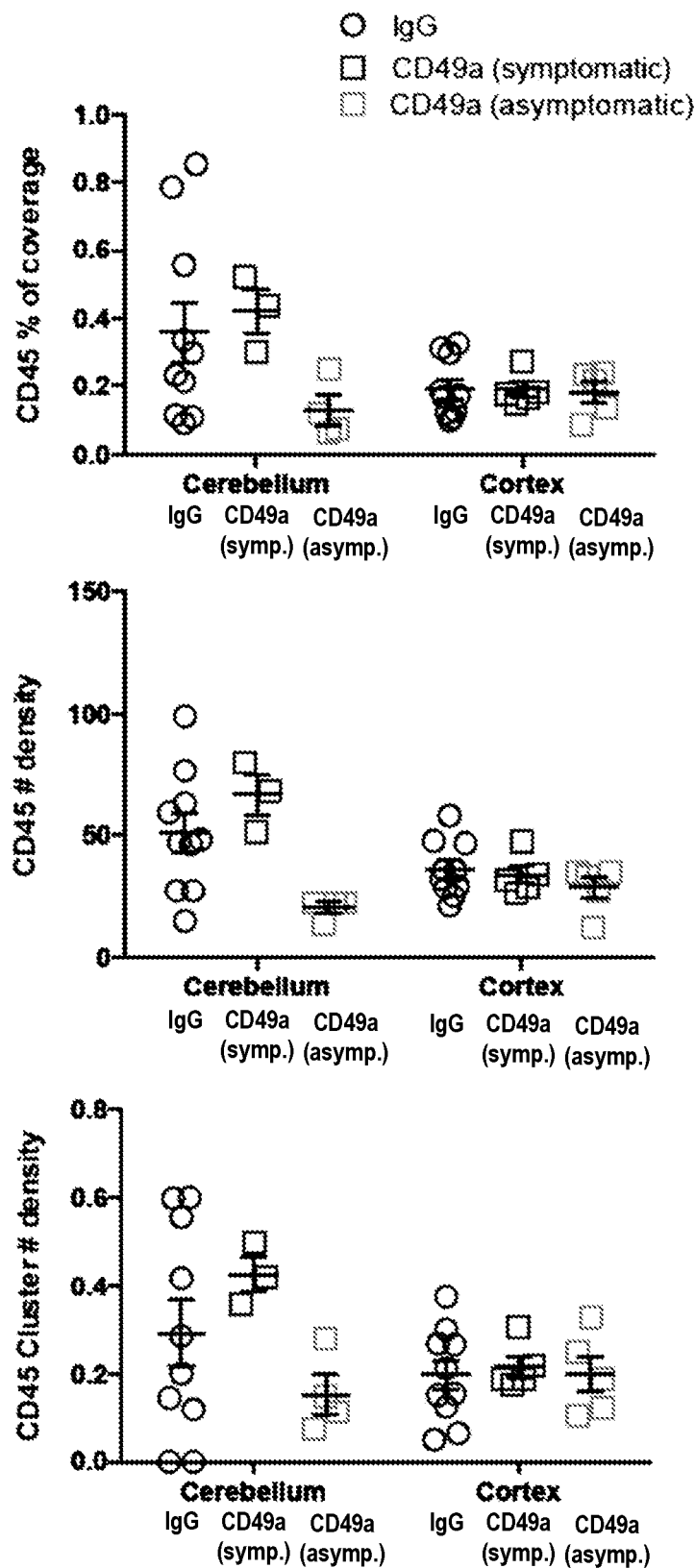
FIGS. 9D-E are each graphs showing CD45+ expression patterns in IgG and CD49a treated mice induced with EAE.
Figure 9E:
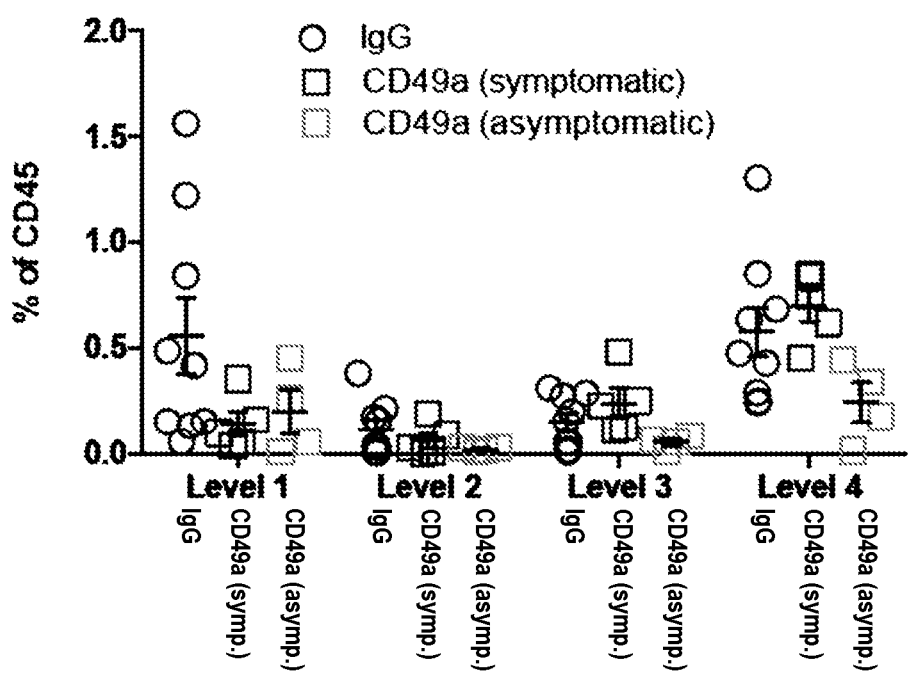

Example 7: CD49a Blockade During EAE Results in Decrease Disease Incidence Without Preventing Immune Cells Infiltration Adult C57B16 mice were immunized with 200 µg of MOG with CFA supplemented with 2 mg/ml of mycobacterium. At D7 post EAE induction, mice were injected i.c.m. with 5 µg of anti-CD49a (or IgG). FIG. 9A shows clinical score of IgG and CD49a treated mice. (mean±s.e.m.; n=36/37 mice/group; p<0.01; repeated measures two-way ANOVA). FIG. 9B shows incidence of clinical symptoms development of IgG and CD49a treated mice. (mean±s.e.m.; n=36/37 mice/group; *p<0.001; Log-rank test). FIG. 9C shows clinical scores of symptomatic IgG and CD49a treated mice (mean±s.e.m.; n=24/35 mice/group). Imaging of CD45+ infiltrate in the cerebellum of IgG and CD49a treated mice induced with EAE showed different patterns of CD45 immune cells in the cerebellum of IgG-treated controls and anti-CD49-treated symptomatic and asymptomatic mice, which are described quantitatively in FIGS. 9D and 9E. FIG. 9D shows quantification of the CD45 coverage, CD45+ cells density and density of CD45 cluster in the cerebellum and cortex of IgG and CD49a treated mice induced with EAE. (mean±s.e.m.; n=3/10 mice/group). FIG. 9E shows quantification of the CD45 coverage in the spinal cord of IgG and CD49a treated mice induced with EAE. (mean±s.e.m.; n=4/9 mice/group).

Thus, administering an inhibitor of CD49a signaling to an EAE subject (a model of MS) in accordance with some embodiments herein delayed the onset of EAE, reduced the incidence of EAE, and improved the clinical score of the EAE subject. Accordingly, it is contemplated that administering an inhibitor of CD49a (such as an antibody or antigen binding fragment thereof that binds specifically to CD49a) in accordance with some embodiments herein can delay the onset of, reduce the incidence of, and/or ameliorate symptoms of MS.

Example 8: Validation of the CD49a-KO Mice

Figure 10A:
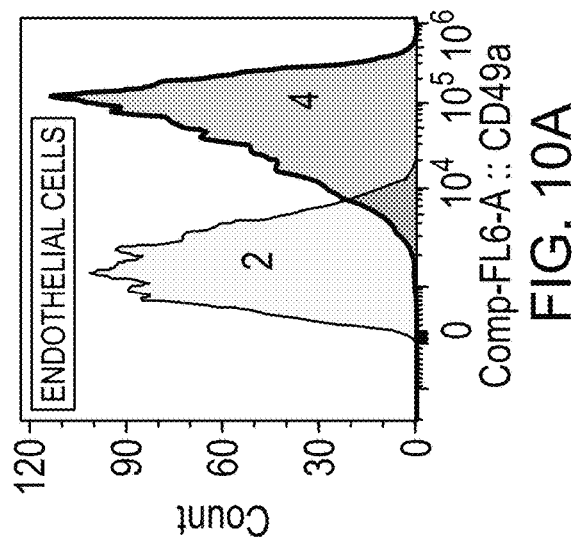
FIGS. 10A-G are each graphs showing cell counts in the meninges of adult WT mice 2 and CD49a KO 4 mice. Shown are endothelial cells (FIG. 10A), ILC I (FIG. 10B), NK cells (FIG. 10C), macrophages (FIG. 10D), ILC (FIG. 10E), and NKT cells (FIG. 10F).
Figure 10B:
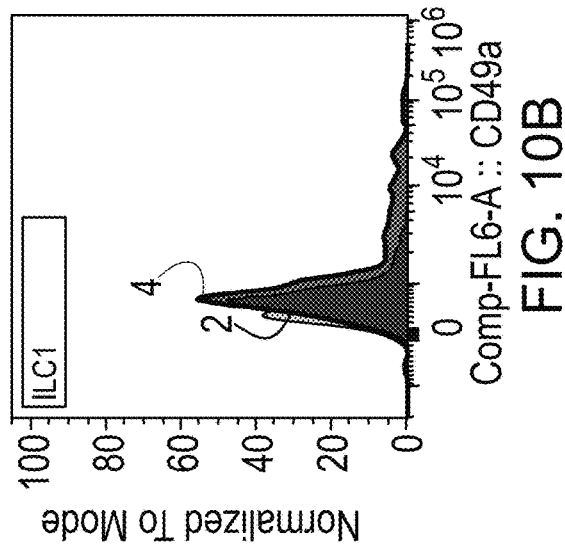
Figure 10C:
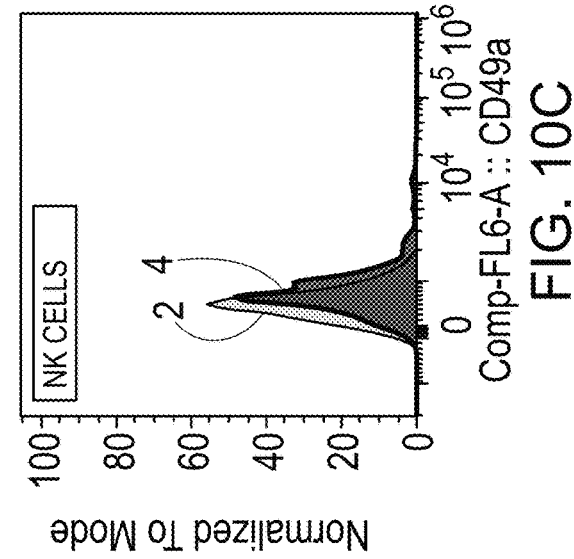
Figure 10D:
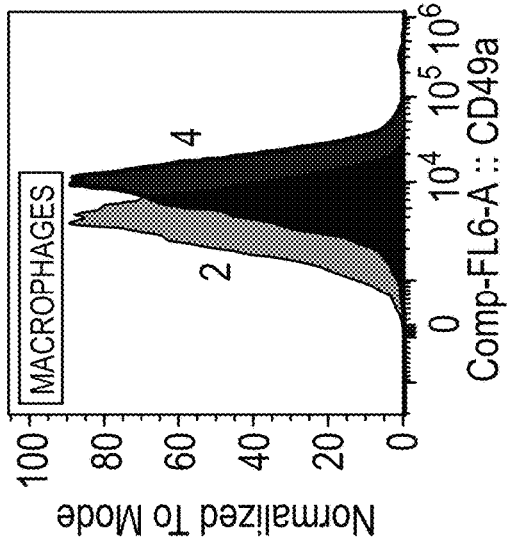
Figure 10E:
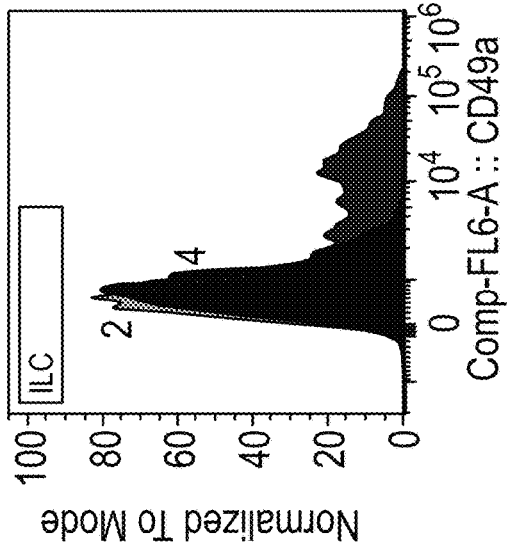
Figure 10F:
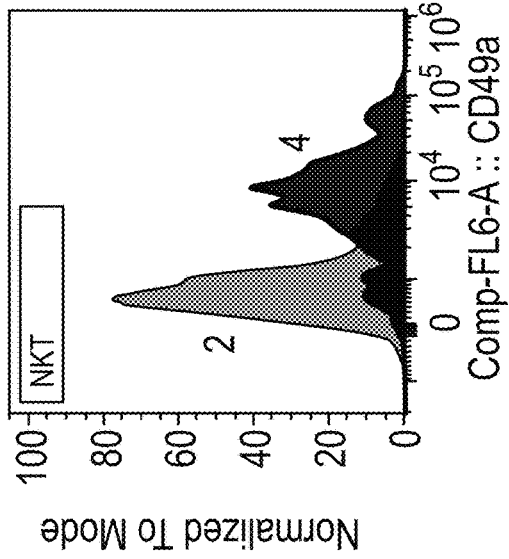
Figure 10G:
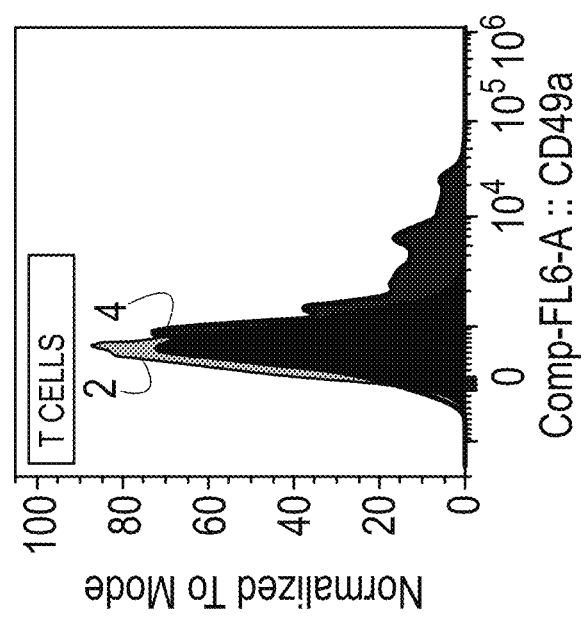

Meninges from adult CD49a WT and CD49a KO mice were harvested and analyzed by FACS. FIGS. 10A-G shows representative histogram of CD49a expression by the indicated cell in CD49a WT mice 2 and CD49a KO mice 4. Shown are endothelial cells (FIG. 10A), ILC I (FIG. 10B), NK cells (FIG. 10C), macrophages (FIG. 10D), ILC (FIG. 10E), and NKT cells (FIG. 10F). Endothelial cells, macrophages, ILC, NKT cells, and T cells were lower in the CD49a knockouts meninges compared to wild type controls. Thus, the knockout data further demonstrate that inhibiting CD49a in accordance with some embodiments herein reduces counts of macrophages, NKT cells, and T cell in the meninges.

Each of the following references is incorporated by reference in its entirety herein.

Louveau, A., Harris, T. H. & Kipnis, J. Revisiting the Mechanisms of CNS Immune Privilege. *Trends Immunol.* 36, 569-577 (2015).

Kipnis, J., Gadani, S. & Derecki, N. C. Pro-cognitive properties of T cells. *Nat. Rev. Immunol.* 12, 663-669 (2012).

Marin, I. & Kipnis, J. Learning and memory . . . and the immune system. *Learn. Mem. Cold Spring Harb. N* 20, 601-606 (2013).

Schwartz, M., Kipnis, J., Rivest, S. & Prat, A. How do immune cells support and shape the brain in health, disease, and aging? *J. Neurosci. Off. J. Soc. Neurosci.* 33, 17587-17596 (2013).

Ransohoff, R. M. & Engelhardt, B. The anatomical and cellular basis of immune surveillance in the central nervous system. *Nat. Rev. Immunol.* 12, 623-635 (2012).

Andersson, U. & Tracey, K. J. Neural reflexes in inflammation and immunity. *J. Exp. Med.* 209, 1057-1068 (2012).

Brynskikh, A., Warren, T., Zhu, J. & Kipnis, J. Adaptive immunity affects learning behavior in mice. *Brain. Behav. Immun.* 22, 861-869 (2008).

Derecki, N. C. et al. Regulation of learning and memory by meningeal immunity: a key role for IL-4. *J. Exp. Med.* 207, 1067-1080 (2010).

Radjavi, A., Smirnov, I., Derecki, N. & Kipnis, J. Dynamics of the meningeal CD4(+) T-cell repertoire are defined by the cervical lymph nodes and facilitate cognitive task performance in mice. *Mol. Psychiatry* 19, 531-533 (2014).

Louveau, A. et al. Structural and functional features of central nervous system lymphatic vessels. *Nature* (2015). doi:10.1038/nature14432

Carbone, F. R. Tissue-Resident Memory T Cells and Fixed Immune Surveillance in Nonlymphoid Organs. *J. Immunol. Baltim. Md.* 1950 195, 17-22 (2015).

Park, C. O. & Kupper, T. S. The emerging role of resident memory T cells in protective immunity and inflammatory disease. *Nat. Med.* 21, 688-697 (2015).

Clark, R. A. Resident memory T cells in human health and disease. *Sci. Transl. Med.* 7, 269rv1 (2015).

Fan, X. & Rudensky, A. Y. Hallmarks of Tissue-Resident Lymphocytes. *Cell* 164, 1198-1211 (2016).

Gardner, H. Integrin α1β1. *Adv. Exp. Med. Biol.* 819, 21-39 (2014).

Chen, Y. et al. CD49a promotes T-cell-mediated hepatitis by driving T helper 1 cytokine and interleukin-17 production. *Immunology* 141, 388-400 (2014).

What is claimed is:

1. A method of treating, preventing, inhibiting, delaying the onset of, or ameliorating multiple sclerosis (MS) or a symptom thereof in a human subject, comprising administering to the subject a therapeutically effective amount of a CD49a-specific antibody, wherein in the CD49a-specific antibody comprises (a) a light chain variable region (VL) comprising the amino acid sequence of SEQ ID NO: 2 and a heavy chain variable region (VH) that has the amino acid sequence of SEQ ID NO: 3.

2. The method of claim 1, wherein the administration of the CD49a-specific antibody is via intracerebroventricular injection.

3. The method of claim 1, wherein the CD49a-specific antibody is administered after the onset of MS.

4. The method of claim 3, wherein the administration of the CD49a-specific antibody after the onset of MS reduces clinical symptoms of MS.

5. The method of claim 1, wherein the MS is treated.

* * * * *